United States Patent
Eckstein et al.

(10) Patent No.: US 8,171,972 B2
(45) Date of Patent: *May 8, 2012

(54) STRIP GUIDE FOR HIGH-SPEED CONTINUOUS APPLICATION OF A STRIP MATERIAL TO A MOVING SHEET-LIKE SUBSTRATE MATERIAL AT LATERALLY SHIFTING LOCATIONS

(75) Inventors: Joseph Allen Eckstein, Sunman, IN (US); Terry Howard Thomas, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 477 days.

This patent is subject to a terminal disclaimer.

(21) Appl. No.: 12/363,002

(22) Filed: Jan. 30, 2009

(65) Prior Publication Data

US 2010/0193139 A1    Aug. 5, 2010

(51) Int. Cl.
*B29C 65/02* (2006.01)
(52) U.S. Cl. ......... 156/496; 156/229; 156/163; 156/164
(58) Field of Classification Search ................ 156/226, 156/496, 229, 163, 164
See application file for complete search history.

(56) References Cited

U.S. PATENT DOCUMENTS

| | | | |
|---|---|---|---|
| 2,689,694 A | 9/1954 | Adamson | |
| 4,515,652 A | 5/1985 | Gimpelson et al. | |
| 4,634,482 A | 1/1987 | Lammers | |
| 4,666,542 A | 5/1987 | Jonckheere | |
| 4,675,016 A | 6/1987 | Meuli et al. | |
| 4,675,068 A | 6/1987 | Lundmark | |
| 4,711,683 A | 12/1987 | Merkatoris | |
| 4,726,874 A | 2/1988 | Vanvliet | |
| 4,735,673 A | 4/1988 | Piron | |
| 4,762,582 A | 8/1988 | De Jonckheere | |
| 4,764,242 A | 8/1988 | Gressick et al. | |
| 4,801,345 A | 1/1989 | Dussaud et al. | |
| 4,842,666 A | 6/1989 | Werenicz | |
| 4,854,984 A | 8/1989 | Ball et al. | |
| 4,915,767 A | 4/1990 | Rajala et al. | |
| 4,917,696 A | 4/1990 | De Jonckheere | |
| 4,917,746 A | 4/1990 | Kons et al. | |
| 4,919,738 A | 4/1990 | Ball et al. | |
| 4,995,928 A | 2/1991 | Sabee | |
| 5,000,806 A | 3/1991 | Merkatoris et al. | |
| 5,080,741 A | 1/1992 | Nomura et al. | |
| 5,171,388 A | 12/1992 | Hoffman et al. | |

(Continued)

FOREIGN PATENT DOCUMENTS

EP    783286 B1    5/2000

(Continued)

OTHER PUBLICATIONS

International Search Report.

*Primary Examiner* — Katarzyna Wyrozebski Lee
*Assistant Examiner* — Vishal I Patel
(74) *Attorney, Agent, or Firm* — William E. Gallagher

(57) ABSTRACT

Disclosed are examples of a strip guide for laterally shifting a longitudinally moving strip material as it enters a joining mechanism that urges the strip material into contact with a moving sheet material, the strip guide comprising a surface over which the strip material passes longitudinally, the surface defining a U-shape.

5 Claims, 15 Drawing Sheets

U.S. PATENT DOCUMENTS

| | | | |
|---|---|---|---|
| 5,213,645 A | 5/1993 | Nomura et al. | |
| 5,275,676 A | 1/1994 | Rooyakkers et al. | |
| 5,342,341 A | 8/1994 | Igaue et al. | |
| 5,389,173 A | 2/1995 | Merkatoris et al. | |
| 5,413,654 A | 5/1995 | Igaue et al. | |
| 5,439,459 A | 8/1995 | Tanji et al. | |
| 5,447,508 A | 9/1995 | Numano et al. | |
| 5,500,075 A | 3/1996 | Herrmann | |
| 5,525,175 A * | 6/1996 | Blenke et al. | 156/161 |
| 5,531,850 A | 7/1996 | Herrmann | |
| 5,545,285 A | 8/1996 | Johnson | |
| 5,622,581 A | 4/1997 | Ducker et al. | |
| 5,660,664 A | 8/1997 | Herrmann | |
| 5,683,531 A | 11/1997 | Roessler et al. | |
| 5,716,478 A | 2/1998 | Boothe et al. | |
| 5,745,922 A | 5/1998 | Rajala et al. | |
| 5,766,411 A | 6/1998 | Wilson | |
| 5,779,689 A | 7/1998 | Pfeifer et al. | |
| 6,069,294 A | 5/2000 | Leclercq et al. | |
| 6,146,430 A | 11/2000 | Tatsuma et al. | |
| 6,171,682 B1 | 1/2001 | Raidel et al. | |
| 6,197,138 B1 | 3/2001 | Mcnichols | |
| 6,197,406 B1 | 3/2001 | Kwok | |
| 6,200,635 B1 | 3/2001 | Kwok | |
| 6,284,081 B1 | 9/2001 | Vogt et al. | |
| 6,287,409 B1 | 9/2001 | Stephany | |
| 6,358,350 B1 | 3/2002 | Glaug et al. | |
| 6,369,291 B1 | 4/2002 | Uchimoto et al. | |
| 6,387,471 B1 | 5/2002 | Taylor et al. | |
| 6,432,242 B1 | 8/2002 | Nielsen et al. | |
| 6,461,430 B1 | 10/2002 | Kwok | |
| 6,463,078 B1 | 10/2002 | Engstrom et al. | |
| 6,531,085 B1 | 3/2003 | Zhou et al. | |
| 6,540,951 B1 | 4/2003 | Zhou et al. | |
| 6,547,915 B2 | 4/2003 | Taylor et al. | |
| 6,548,147 B1 | 4/2003 | Raidel et al. | |
| 6,562,015 B1 | 5/2003 | Wilson | |
| 6,569,275 B1 | 5/2003 | Popp et al. | |
| 6,585,841 B1 | 7/2003 | Popp et al. | |
| 6,589,149 B1 | 7/2003 | Vaneperen et al. | |
| 6,602,238 B2 | 8/2003 | Takei et al. | |
| 6,605,173 B2 | 8/2003 | Glaug et al. | |
| 6,620,276 B1 | 9/2003 | Kuntze et al. | |
| 6,623,468 B2 | 9/2003 | Shimoe | |
| 6,808,582 B2 | 10/2004 | Popp et al. | |
| 6,878,647 B1 | 4/2005 | Rezai et al. | |
| 6,884,494 B1 | 4/2005 | Curro et al. | |
| 6,890,630 B2 | 5/2005 | Franklin et al. | |
| 6,895,649 B2 | 5/2005 | Kojo et al. | |
| 6,905,565 B2 | 6/2005 | Shimoe | |
| 6,962,749 B2 | 11/2005 | Zhou et al. | |
| 6,964,720 B2 | 11/2005 | Schneider et al. | |
| 7,037,569 B2 | 5/2006 | Curro et al. | |
| 7,045,031 B2 | 5/2006 | Popp et al. | |
| 7,048,991 B2 | 5/2006 | Franklin et al. | |
| 7,087,287 B2 | 8/2006 | Curro et al. | |
| 7,097,725 B2 | 8/2006 | Yoneoka et al. | |
| 7,179,343 B2 | 2/2007 | Vaneperen et al. | |
| 7,189,448 B2 | 3/2007 | Raidel et al. | |
| 7,195,684 B2 | 3/2007 | Satoh | |
| 7,197,049 B2 | 3/2007 | Engstrom et al. | |
| 7,211,531 B2 | 5/2007 | Schneider et al. | |
| 7,223,818 B2 | 5/2007 | Autran et al. | |
| 7,227,051 B2 | 6/2007 | Mitsui et al. | |
| 7,270,861 B2 | 9/2007 | Broering et al. | |
| 7,307,031 B2 | 12/2007 | Carroll et al. | |
| 7,410,683 B2 | 8/2008 | Curro et al. | |
| 2002/0023706 A1 | 2/2002 | Vogt et al. | |
| 2002/0153086 A1 | 10/2002 | Alper et al. | |
| 2003/0010423 A1 | 1/2003 | Nakakado et al. | |
| 2003/0116257 A1 | 6/2003 | Franklin et al. | |
| 2003/0144643 A1 | 7/2003 | Jarpenberg et al. | |
| 2004/0108043 A1 | 6/2004 | Otsubo | |
| 2005/0000628 A1 | 1/2005 | Norrby | |
| 2005/0145322 A1 | 7/2005 | Hoffman et al. | |
| 2006/0161131 A1 | 7/2006 | Kurata et al. | |
| 2006/0185135 A1 | 8/2006 | Yamamoto et al. | |
| 2007/0035055 A1 | 2/2007 | Gee et al. | |
| 2007/0167929 A1 | 7/2007 | Fossum et al. | |
| 2007/0218425 A1 | 9/2007 | Gatti | |
| 2007/0249254 A1 | 10/2007 | Mansfield | |
| 2007/0293111 A1 | 12/2007 | Mansfield | |
| 2008/0300565 A1 | 12/2008 | Takahashi et al. | |

FOREIGN PATENT DOCUMENTS

| | | | |
|---|---|---|---|
| EP | 858791 B1 | 8/2002 | |
| EP | 1 842 516 B1 | 11/2009 | |
| FR | 1542271 A | 10/1968 | |
| GB | 707497 A | 4/1954 | |
| JP | 59204902 A | 11/1984 | |
| JP | 8132576 A | 5/1996 | |
| JP | 8280740 A | 10/1996 | |
| WO | WO-97/00654 A1 | 1/1997 | |
| WO | WO-2008/149761 A1 | 12/2008 | |

* cited by examiner

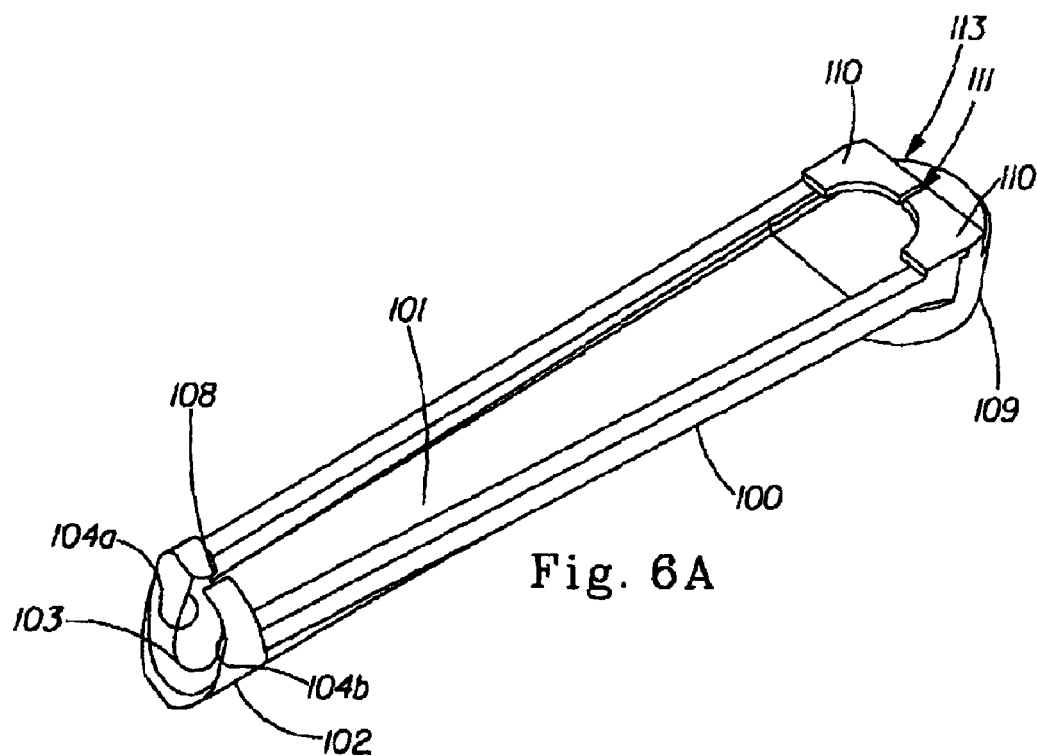
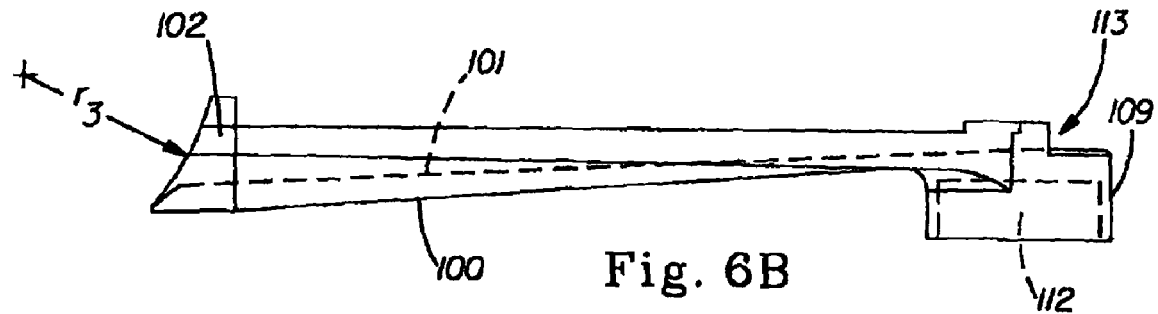
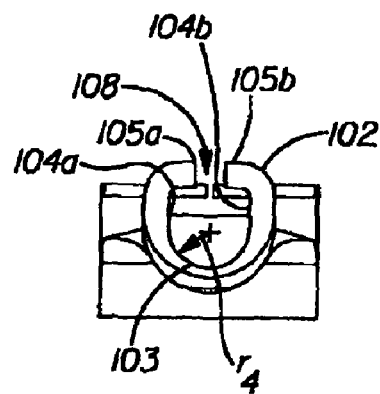 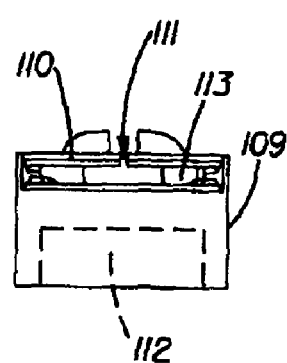

STRIP GUIDE FOR HIGH-SPEED CONTINUOUS APPLICATION OF A STRIP MATERIAL TO A MOVING SHEET-LIKE SUBSTRATE MATERIAL AT LATERALLY SHIFTING LOCATIONS

FIELD OF THE INVENTION

This invention relates to a system, components thereof, and method for continuously applying and affixing a strip material to a sheet-like substrate material moving longitudinally through a manufacturing line, at laterally shifting locations on the substrate material. More particularly, the present invention relates to a system and components that continuously draw respective strip material and sheet-like substrate material from continuous supplies, and laterally shift the strip material across the machine direction of the substrate material as the two materials enter a joining mechanism that affixes the strip material onto the substrate material. The invention also relates to a system, components thereof, and method for continuously regulating the strain in a longitudinal material as it enters a joining mechanism.

BACKGROUND OF THE INVENTION

Currently, wearable articles such as disposable diapers, disposable training pants, disposable adult incontinence garments and the like are constructed of various types of sheet- or strip-like materials. These materials may include nonwoven webs formed of synthetic polymer and/or natural fibers ("nonwovens"), polymeric films, elastic strands, strips or sheets, or assemblies or laminates of these materials. In a typical article, nonwovens and/or laminates of various types form at least one component of an outer garment-facing layer ("backsheet"), an inner body-facing layer ("topsheet") and various internal layers, cuffs, envelopes or other features, depending upon the particular features of the product. The component sheet- or strip-like materials are usually supplied in the form of large continuous rolls, or alternatively, boxes of continuous longitudinal sheet or strip material gathered and folded transversely in accordion fashion.

The articles are typically manufactured on relatively complex manufacturing lines. Supplies of the required materials are placed at the front of each line. As a line requires the materials for the manufacture of articles, it continuously draws the materials longitudinally from their respective supplies. As a particular material is drawn from the supply and proceeds through the line to be incorporated into final product, it may be flipped, shifted, folded, laminated, welded, stamped, embossed, bonded to other components, cut, etc., ultimately being fashioned by the machinery into an incorporated part of the finished product. All of this happens at the economically-required production rate, e.g., 450 or more product items per line per minute. Generally, for purposes of economy, increasing the production rate is an ever-present objective.

A new design for a wearable absorbent article such as a disposable diaper, training pant or adult incontinence undergarment has been developed. The article has features that give it an underwear-brief-like fit, feel and appearance, which consumers may find appealing. Among the features that give it this fit, feel and appearance are elastic bands about respective leg openings that encircle the wearer's legs. The elastic bands may be formed of, for example, one or more strands or strips of an elastic material such as spandex, bonded with one or more strips of nonwoven or film material to form a band-like elastic strip material. On the subject wearable absorbent article design, these elastic bands are affixed or bonded to the outer surface of a substrate outer cover (backsheet) material, with the lower side edges of each of the elastic bands being substantially coterminous with each of the respective leg openings to create a neatly finished, banded appearance. The elastic strip material may be longitudinally strained prior to affixation to the backsheet material, whereby subsequent relaxation of the elastic strip material causes the backsheet material to gather about the leg openings, for improved fit and comfort.

To date, the subject design has been produced only by hand manufacturing or limited machine-assisted manufacturing techniques, at rates that are too low for economically feasible production of the design as a viable (i.e., competitively priced) consumer product.

Among the problems that the design presents is determining how the elastic strip material can be accurately placed and affixed to the substrate backsheet material at locations required by the design and at economically feasible production speeds, e.g., 450 items or more per minute, in a manner that is reliable, minimizes waste, and maximizes consistency and quality of the band placement and affixing process. It is envisioned that strip material will be applied and affixed to substrate backsheet material at laterally varying design-required locations, as the substrate material moves longitudinally through the manufacturing line at production speed. Under these circumstances, one particular problem lies in determining how to rapidly and repeatedly laterally shift back and forth the point at which such strip material enters a joining/bonding mechanism, without causing the typically pliable, cloth-like strip material to "rope" (longitudinally fold or bunch over on itself) before it enters the joining/bonding mechanism.

A potential associated problem lies in regulating the strain of the elastic strip material as it is affixed to a substrate material. If elastic strip material under longitudinal strain is shifted laterally between two points at which it is gripped, this will cause variation in the strain. Thus, shifting elastic strip material laterally as it is being affixed to substrate material may result in variation in the longitudinal strain of the strip material as affixed to the substrate. In some circumstances this may have undesirable effects.

It would be advantageous if a system, apparatus and method existed to address the problems referenced above.

SUMMARY OF THE INVENTION

In one example, the invention may include a strip guide for laterally shifting a longitudinally moving strip material as it enters a joining mechanism that urges the strip material into contact with a moving sheet material, the strip guide comprising a surface over which the strip material passes longitudinally, the surface defining a U-shape.

BRIEF DESCRIPTION OF THE DRAWINGS

FIGS. 6A-6D are perspective, side, front and rear views, respectively, of a strip guide arm;

DETAILED DESCRIPTION OF EXEMPLARY EMBODIMENTS

Figure 1:
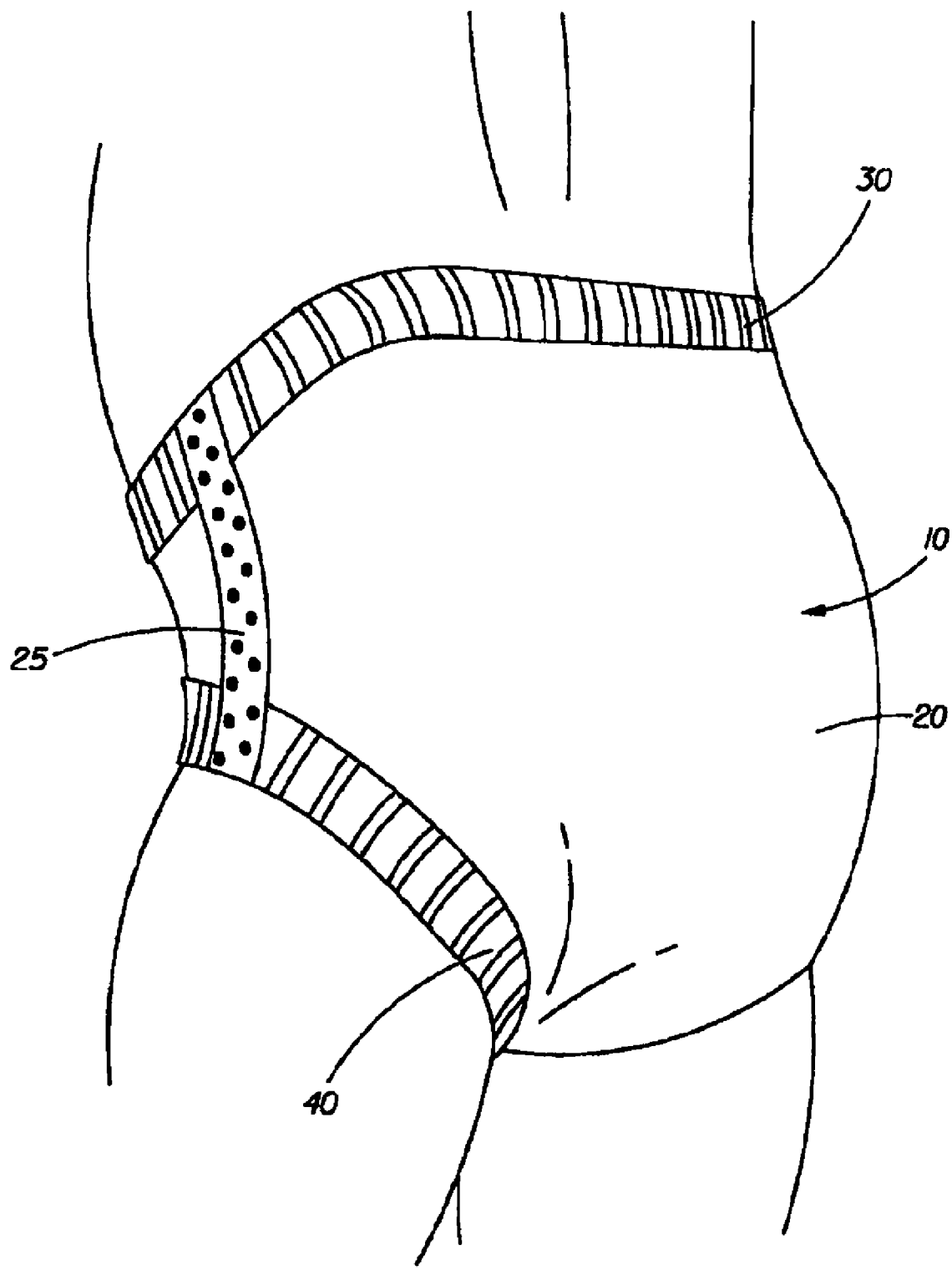
FIG. 1 is a perspective sketch of a wearable article as it may be worn by a person.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

DEFINITIONS

For purposes of this description, the following terms have the meanings set forth below:

Connected: With respect to a relationship between two mechanical components, unless otherwise specified, "connected" means that the components are directly physically connected to each other, or indirectly physically connected to each other through intermediate components. Unless otherwise specified, "connected" is not meant to imply or be limited to a connection that causes the components to become immovably fixed with respect to each other.

Continuous supply: With respect to a supply of sheet- or strip-like materials forming components of a product, means a length of such material on a roll, or folded accordion-fashion ("festooned"), whereby the material may be drawn therefrom in longitudinal or linear fashion by machinery, to manufacture a quantity of items or products from one such length. Noting that such lengths are not of infinite length, "continuous supply" is not intended to exclude, but also is not intended to necessarily mean, a supply that is infinite or without end.

Downstream: With respect to components of a manufacturing line, relates to the direction or orientation of forward travel of materials through the manufacturing line toward completion of a product.

Lateral (and forms thereof): With respect to the machine direction, means transverse to the machine direction.

Longitudinal (and forms thereof): With respect to a feature of a mechanical system component or component of a product, means substantially parallel to or along the line of the longest dimension of the component.

Machine direction: With respect to a component of a product, refers to any line along the component substantially parallel to the direction of forward travel of the component through the manufacturing line toward completion of a product.

Servo motor: Any rotary electric motor having a rotating output drive shaft, which motor is adapted to be controlled such that the drive shaft can be caused to rotate (within performance limits) at constant, varying and continuously varying, user-selected or user-programmed: angular velocity, angular acceleration/deceleration, rotational direction and/or rotational stop or reversal position.

Strip material: Means any band-like, strip-like, strap-like, or ribbon-like material that, when longitudinally extended, has a greatest longitudinal dimension, and a cross section in a plane substantially perpendicular to the longitudinal dimension, the cross section having an aspect ratio, or a ratio of width to thickness, equal to or greater than about 2.5. The term includes but is not limited to materials that have substantially rectangular or substantially oval cross sections, as well as elongated but irregular cross sections. The term includes but is not limited to materials that are natural or synthetic, cloth or cloth-like, woven or nonwoven, or film, and includes but is not limited to materials that are inelastic, elastic and/or elasticized. The term includes but is not limited to homogeneous strip-like materials, fibrous strip-like materials and assembled or composite strip-like materials, such as laminates or other assemblies of differing materials such as an assembly of one or more elastic strands or strips situated next to one, or between two or more, strips of film, cloth or nonwoven material.

Upstream: With respect to components of a manufacturing line, relates to the direction or orientation opposite that of forward travel of materials through the manufacturing line toward completion of a product.

Example of Wearable Article and Manufacturing Problems Presented

An example of a product such as wearable article 10 as it may be worn by a person is depicted in FIG. 1. The wearable article 10 has a garment-facing outer cover or backsheet 20, a waistband 30 and a pair of legbands 40. The backsheet 20 may be elastic or stretchable, and may be formed at least in part of a nonwoven or laminate of a nonwoven and a polymeric film. Various possible examples of backsheet materials are described in U.S. Pat. Nos. 6,884,494; 6,878,647; 6,964,720; 7,037,569; 7,087,287; 7,211,531; 7,223,818; 7,270,861; 7,307,031; and 7,410,683; and in U.S. Published Applications, Publication Nos. 2006/0035055; 2007/0167929; 2007/0218425; 2007/0249254; 2007/0287348; 2007/0293111; and 2008/0045917.

In order that they may contribute to the desired fit, feel and appearance, it may be desirable to form waistband 30 and legbands 40 at least partly of an elastic material such as an elastic strip material. The elastic strip material may be formed, for example, by sandwiching one or more strands or strips of elastic polymer material between, for example, two outer strips of nonwoven and/or film. In one example, the elastic strip material may be formed by first longitudinally stretching the one or more strands or strips of elastic polymer material, and then bonding the two outer strips of nonwoven and/or film on either side thereof to sandwich the stretched elastic polymer material therebetween. When the elastic polymer material is allowed to relax it will cause the bonded strips of nonwoven and/or film to ruffle transversely. The resulting transverse rugosities will comprise longitudinally gathered material which accommodates longitudinal stretching along with the elastic strip material. In a particular example, an elastic strip material may be formed of a plurality, for example, three to nine, strands of elastomeric material such as spandex, sandwiched between two outer strips of nonwoven and/or film bonded together, wherein the elastomeric strands are stretched prior to bonding, resulting in an elastic strip material having transverse rugosities of outer material. In another example, an elastic strip material may be formed of a strip of elastic film, or one or more elastic strands, bonded to a single strip of nonwoven or film, on one side only. In another example, an elastic strip material may be formed of a single strip of elastic film material, or single strip of nonwoven material having desired inherent elastic properties.

For purposes of balancing objectives of economy, appearance, fit and comfort, the strip material for the waistband 30 may be, for example, approximately 10-50 mm wide, or approximately 10-35 mm wide, or approximately 10-30 mm wide, or even approximately 10-25 mm wide. Using typical materials, the strip material for the waistband may be, for example, approximately 1-4 mm thick, or even approximately 1.5-2.5 mm thick, in the relaxed and uncompressed state. Thus, the particular strip material used for the waistband may have a cross-section substantially perpendicular to its longest longitudinal dimension, the cross section having an aspect ratio within a broad range of approximately 10:4 (2.5) to 50:1 (50), within a narrow range of approximately 10:4 (2.5) to 25:1 (25), or within any intermediate ranges calculated from the width and thickness ranges set forth above.

For purposes of balancing objectives of economy, appearance, fit and comfort, the strip material for the legbands 40 may be, for example, approximately 10-30 mm wide, or approximately 10-25 mm wide, or approximately 10-20 mm wide, or even approximately 15-20 mm wide. Using typical materials, the strip material for the legbands may be, for example, approximately 1-4 mm thick, or even approximately 1.5-2.5 mm thick, in the relaxed and uncompressed state. Thus, the particular strip material used for the legbands may have a cross-section perpendicular to its longest longitudinal dimension, the cross section having an aspect ratio within a broad range of approximately 10:4 (2.5) to 30:1 (30), within a narrow range of approximately 15:4 (3.75) to 20:1 (20), or within any intermediate ranges calculated from the width and thickness ranges set forth above.

In one example, an elastic strip material of which elastic legbands 40 and/or waistband 30 may be formed may be longitudinally strained prior to being affixed to backsheet 20, and affixed to backsheet 20 while in the strained state. Following affixation to backsheet 20 and completion of the article, relaxation of waistband 30 and/or legbands 40 will cause the waist and/or leg openings in the article to gather so as to fit more snugly and comfortably about the waist and legs of a wearer.

Figure 2:
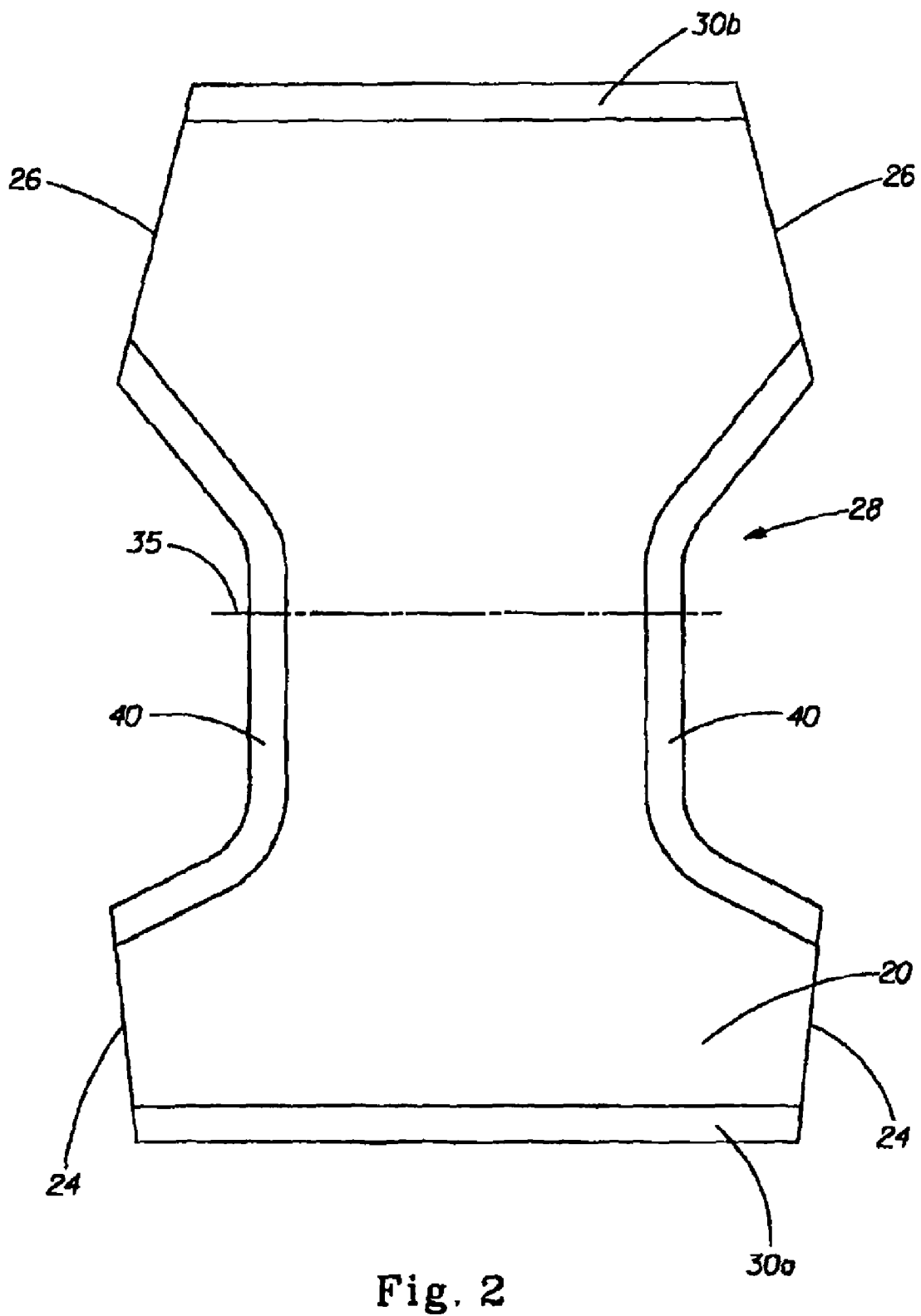
FIG. 2 is a plan view of an outer chassis component of a wearable article such as that shown in FIG. 1, shown laid flat, outside (garment-facing) surface facing the viewer, prior to completion of the wearable article.

FIG. 2 is a plan view of the garment-facing side of outer chassis 28 of a wearable article such as depicted in FIG. 1, laid flat, prior to final assembly, with affixed elastic strip material. Outer chassis 28 includes backsheet 20 with affixed elastic front and rear waistband portions 30a, 30b and legbands 40. To form completed article 10 (FIG. 1), outer chassis 28 (FIG. 2) may be folded laterally at or about lateral line 35, garment-facing side out, to bring front waist edges 24 into overlapping contact with rear waist edges 26. The respective overlapping waist edge pairs may then be affixed together in any suitable manner, such as by compression bonding, adhesive bonding, ultrasonic bonding, etc., to form side seams 25 (FIG. 1).

Figure 3:
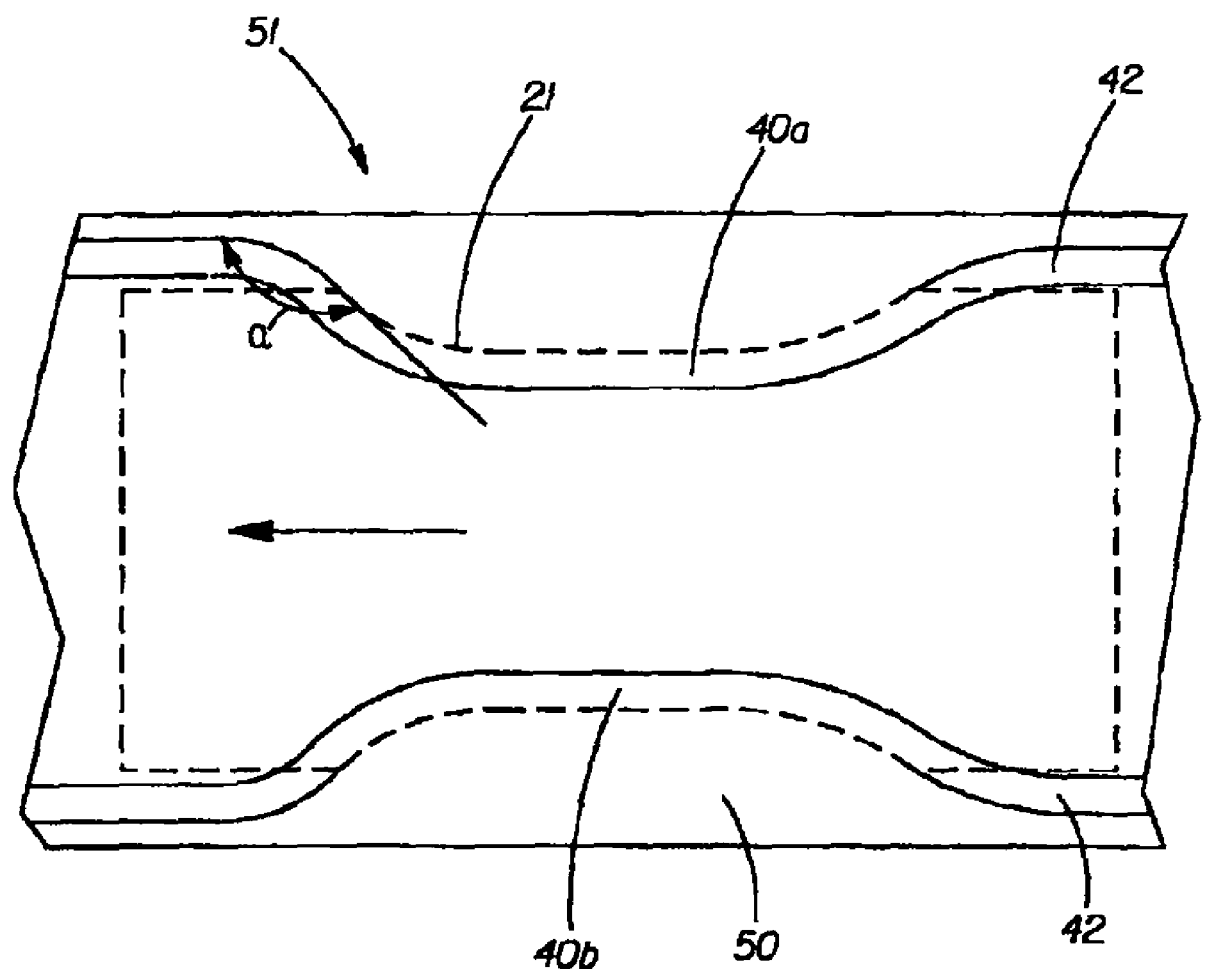
FIG. 3 is a plan view of a partially completed portion of material from which an outer chassis component such as that shown in FIG. 2 may be cut.

Outer chassis 28 may be formed by cutting the design profile of the outer chassis from a continuous sheet of material having elastic strip material already affixed thereto, in the required locations, in upstream processes. FIG. 3 depicts a plan view of a partially completed portion 51 of an outer chassis, formed from a continuous supply of substrate backsheet material 50, with continuous lengths of strip material 42 affixed thereto, as the portion may appear in the manufacturing line following affixation of the strip material 42 to the backsheet material 50. Following affixation of strip material 42 to backsheet material 50 in the configuration shown in FIG. 3 (and, possibly, application of additional elastic strip material (not shown) to form a waistband), partially completed portion 51 may be cut along backsheet design profile 21 (indicated by dashed line in FIG. 3) to create an outer chassis 28 (FIG. 2).

The present invention might be deemed useful for any purpose that includes applying a strip material to a substrate material in laterally varying locations on the substrate material. Thus, in one example, the present invention may be deemed useful in connection with the location, application and affixation of a strip material to a substrate material to form a product or a portion thereof, such as, for example, partially completed portion 51 (FIG. 3) of an outer chassis of a disposable wearable article. The present invention may be deemed particularly useful for this purpose at production speeds exemplified by a disposable wearable article manufacturing line. A typical manufacturing line of the kind used to manufacture wearable articles of the kind described may produce 450 or more finished product items per minute. At 450 items per minute, backsheet material 50 may move longitudinally through the line at approximately 206 meters per minute in a machine direction as indicated by the arrow in FIG. 3. Referring to FIG. 3, equipment is required that laterally shifts strip material 42 for affixing to a substrate at required locations on a repeating basis at the corresponding rate, e.g., of 450 cycles per minute (7.5 cycles per second) or more. The equipment should be able to substantially accurately locate strip material 42 in laterally varying locations such as shown in FIG. 3, and then affix the strip material 42 to the backsheet material 50 in those locations. Also, as previously mentioned, it may be desired to longitudinally strain strip material 42 prior to affixation to backsheet material 50, and to be able to locate and affix the strip to the backsheet material in the strained condition.

For purposes such as those described herein it may be desirable that strip material 42 be applied and affixed to substrate backsheet material 50 in a flat condition, which helps provide a leg band that is of uniform width (e.g., the width of the strip) and thickness, and lies flat on the substrate material. It also may be desirable that strip material 42 be applied by a method that minimizes a decrease in applied strip width that may result in "contour error". Unacceptable contour error may result from laterally shifting a strip material, as it is being drawn through a nip point between rollers, so abruptly that the nip point does not have sufficient time to shift with the lateral movement, such that the strip is drawn askew.

Under certain manufacturing conditions, a pliable strip material may, even under longitudinal tension, exhibit a tendency to longitudinally fold or bunch over onto itself, or "rope," as machine components shift it laterally at required manufacturing speeds. This problem is believed to be characteristic of relatively pliable strip-like materials. Without intending to be bound by theory, it is believed that for any particular strip-like material, the problem increases along with increasing width-to-thickness ratio (cross-sectional aspect ratio). It is believed that the problem may begin to become significant with pliable materials of the nature discussed herein when they have cross-sectional aspect ratios of approximately 2.5 or greater. As cross-sectional aspect ratio for a given material increases, the problem becomes more significant. It is believed that the problem also becomes more significant with increasing pliability across the width of the material (increasing flexibility along longitudinal lines). It is also believed that the problem becomes more significant with a decrease of longitudinal tension in the material. Additionally, air resistance/friction may contribute to roping when attempting to rapidly shift a free span of strip material laterally through open air at required manufacturing speeds. If a free span of pliable strip material is shifted laterally at high enough speeds through open air, friction with the air may cause the span to twist and/or rope erratically. If strip material 42 is roped as it enters a joining mechanism to be affixed to backsheet material 50, non-uniform leg bands having defects in width, thickness, placement, feel and/or appearance are among several possible undesirable results.

A combination of manufacturing line components including a guide upstream of a joining mechanism that urges and affixes a strip material and a substrate sheet material together, is described below. The components also may include a mechanism for regulating the strain in the strip material as it enters the joining mechanism. It is believed that components in the combination, and the combination, are embodiments of components and a system that may be effective at continuously affixing strip material to substrate sheet material at laterally varying locations relative to the machine direction, at speeds that may be required for manufacturing, while reducing or avoiding the problem of roping of the strip material described in more detail above. Embodiments of the strain regulation mechanism described may enable effective regulation of the strain in the strip material as it is affixed to the substrate sheet material.

Figure 4:
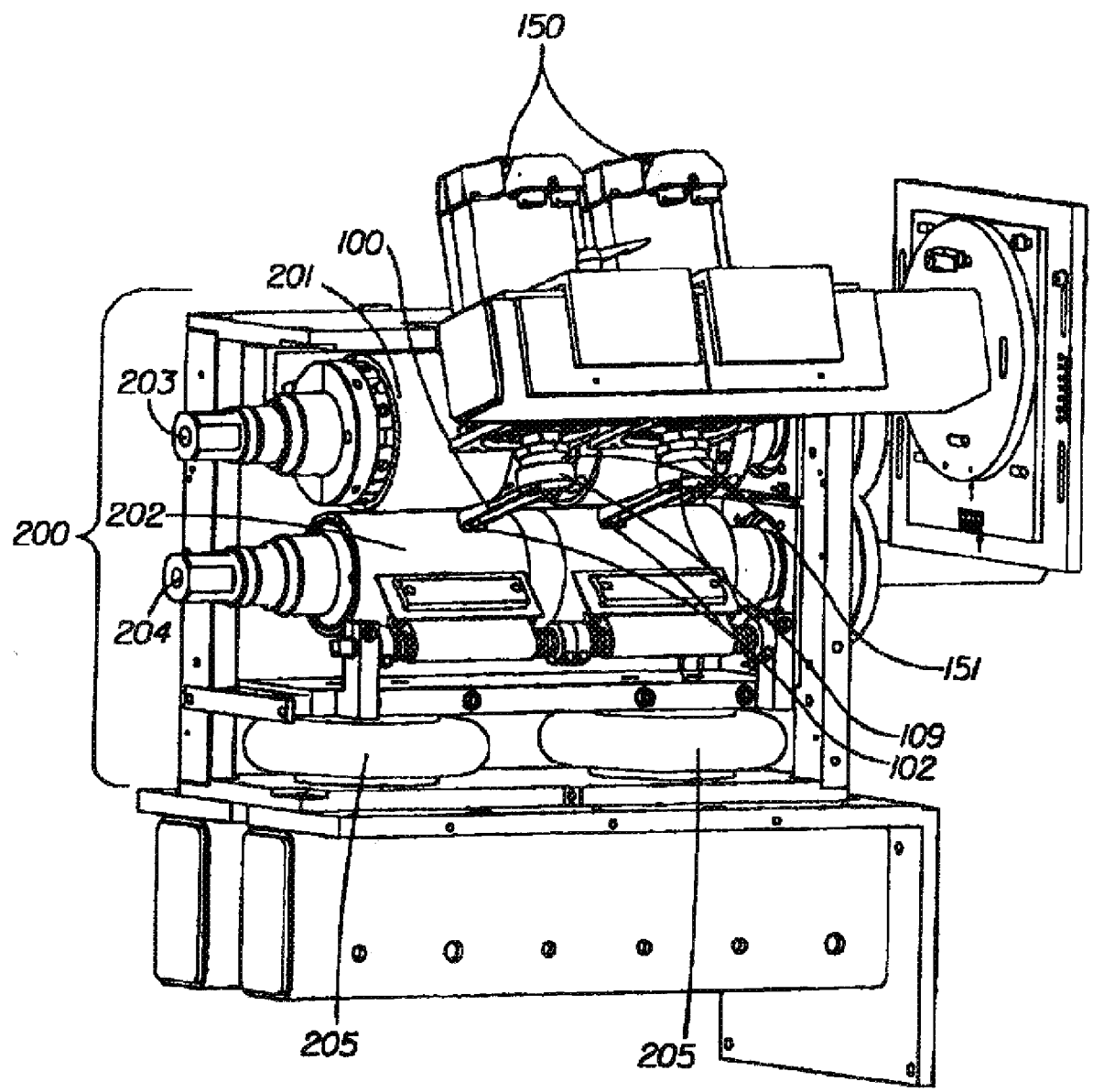
FIG. 4 is a perspective view of components of a system including a pair of strip guide arms and a joining mechanism.

Example of Combination of Manufacturing Line System and Components for Locating and Affixing Strip Material to Sheet Material FIG. 4 is a perspective drawing depicting an example of an arrangement of manufacturing line components. The components may include at least one servo motor 150 having rotatable drive shaft 151. Strip guide arm 100 may be mounted to drive shaft 151 via coupling collar 109. Coupling collar 109 may have drive shaft cavity 112 therein (further described below and depicted in FIGS. 6B, 6D), to receive the end of drive shaft 151.

Coupling collar 109 may be mounted to the end of drive shaft 151 in any suitable manner that prevents substantial rotational slippage/movement of strip guide arm 100 relative to drive shaft 151, including, for example, by welding, press-fitting, keying, splining, set screw(s), etc. However, welding and other devices for mounting that involve potential alteration, modification, damage or destruction to draft shaft 151 and/or servo motor 150 may in some circumstances be deemed undesirable for reasons that may include added complexity and expense of system assembly, and potential complication or frustration of replacement of a worn or broken strip guide arm 100 without having to also repair or replace servo motor 150. Devices such as set screws may be unreliable in that stress and vibration during operation may cause them to work loose or fail. Thus, one example includes a taper locking collar as a device for mounting coupling collar 109 to drive shaft 151. A suitable example of such a taper locking collar is a TRANTORQUE keyless bushing available from Fenner Drives, Leeds, UK.

Examples of suitable servo motors include servo motors designated MPL-B330P and MPL-B4560F, available from Rockwell Automation, Inc., Milwaukee, Wis. The programming of the selected servo motor, to effect lateral location of the strip material 42 relative to backsheet material 50 and create the partially completed portion 51, will be directed by the particular article design.

A strip guide 102 may be situated at a downstream location on strip guide arm 100. The components may be arranged such that strip guide 102 is upstream of a joining mechanism 200. In the example shown in FIG. 4, joining mechanism 200 may include first and second joining rollers 201, 202 that rotate about axles 203, 204 situated along substantially parallel axes. Examples of suitable joining mechanisms utilizing rollers are described in, for example, U.S. Pat. Nos. 4,854,984 and 4,919,738, issued to Ball et al. In these types of mechanisms, a first joining roller 201 may have on its surface one or more protuberances of substantially uniform height arranged in one or more lines or patterns. First joining roller 201 and second joining roller 202 may be urged together by one or more actuators such as bellows-type pneumatic actuators 205 acting directly or indirectly on one or both of axles 203, 204, to provide and regulate compression under the protuberances of strip and sheet materials passing together through the nip between the rollers, in the manner described in the aforementioned patents.

A joining mechanism utilizing compression as the primary means of creating bonds, such as, but not limited to, the mechanism described in the aforementioned patents, provides bonding of respective sheet-like or strip-like polymeric materials through rapid compression of the respective materials together beneath the protuberances, along the roller nip line. Without intending to be bound by theory, it is believed that rapid compression beneath the protuberances causes the respective materials to be rapidly deformed and partially expressed together from beneath the protuberances, to form structures of entangled or combined material beneath and/or around the protuberances. Welds or weld-like structures at or about the protuberances result. In some circumstances compression bonding provides advantages, including relative simplicity and cost effectiveness. It may reduce or eliminate the need for more complex joining and bonding systems that rely upon, for example, adhesives and mechanisms to handle and apply them, or weld-bonding systems that require a heat source, ultrasonic wave source, etc. Without intending to be bound by theory, it is believed that these advantages are substantially independent of variations in line speeds in at least some circumstances, including line speeds within currently known economically and technically feasible ranges for manufacture of disposable diapers and training pants.

Figure 5:
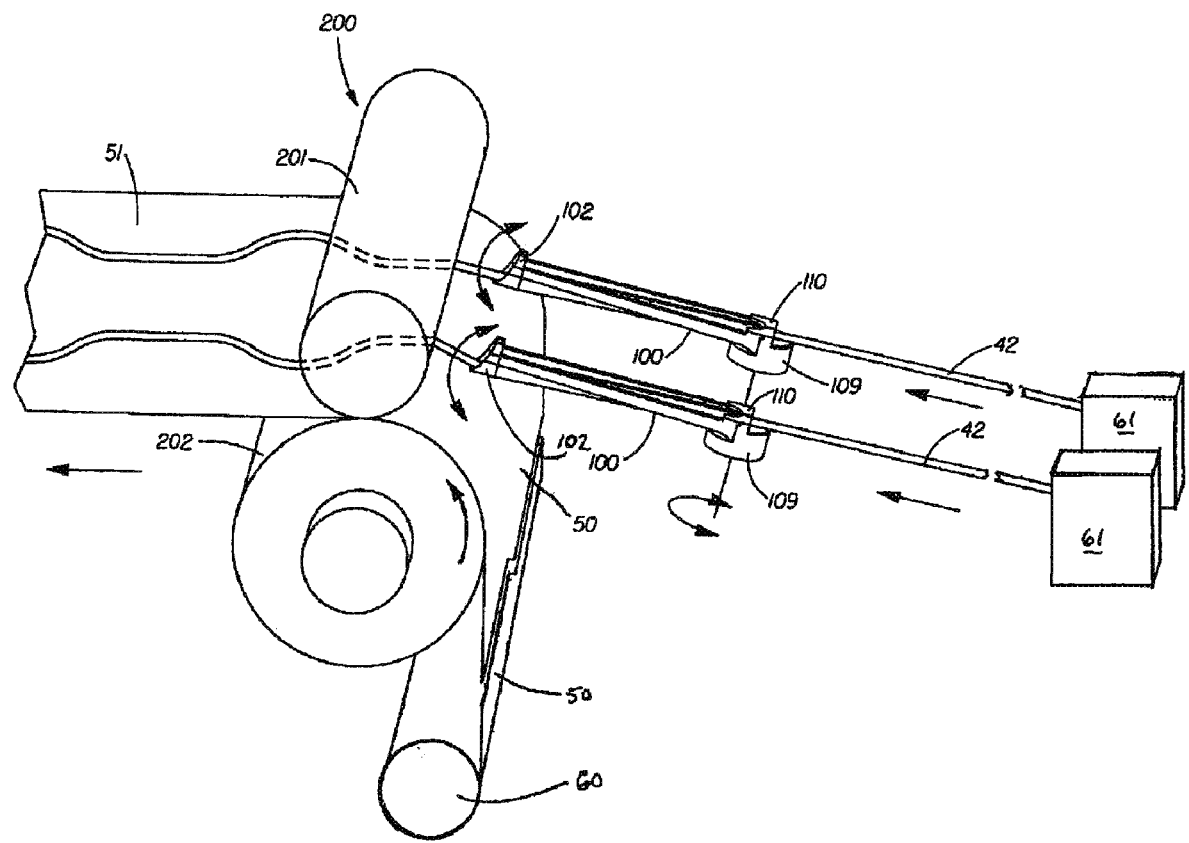
FIG. 5 is a schematic view of a pair of strip guide arms shown guiding strip material into a pair of joining rollers.

FIG. 5 is a schematic depiction of how an arrangement of components such as that shown in FIG. 4 may be operated to affix a strip material to a substrate material. Substrate backsheet material 50 and one or more strips of strip material 42 may be drawn longitudinally from respective supplies 60, 61 toward joining mechanism 200 in the respective machine directions indicated by the arrows. Strip material 42 as selected for the particular application may have a cross-sectional aspect ratio such as that described in the preceding example of a wearable article. Joining mechanism 200 may include first and second joining rollers 201, 202. Upstream of joining mechanism 200, the one or more strips of strip material 42 move along one or more strip guide arms 100. As they move along the strip guide arms 100, strips of strip material 42 may be slidably retained at upstream and downstream locations on strip guide arms 100 by, respectively, strip retainer extensions 110 and strip guides 102. The system may be designed and equipped to provide compression bonding of strip material 42 to backsheet material 50 as noted above. In another example, an adhesive may be applied to strip material 42 upstream of joining mechanism 200, and joining mechanism 200 may press strip material 42 against substrate backsheet material 50 to form an adhesive bond therebetween. In this latter example, joining mechanism 200 also may comprise joining rollers 201, 202, which serve to urge and compress strip material 42 and backsheet material 50 together to form the adhesive bond.

Referring to FIGS. 4 and 5, the one or more strip guide arms 100 may have coupling collars 109 mounted to the rotatable drive shaft(s) 151 of one or more servo motors 150. The one or more servo motors 150 may be operated by suitable programming to pivot guide arms 100 back and forth such that strip guides 102 move laterally (in respective arcs along paths of rotation) across the machine direction, to cause strip material 42 to be laterally shifted and varyingly located with respect to the machine direction of the substrate backsheet material 50 as it enters the joining mechanism 200, as required by the article design. Joining mechanism 200 then may affix strip material 42 to backsheet material 50 at the required locations, resulting in a completed portion 51 (also shown in FIG. 3 and described above) exiting joining mechanism 200 and moving downstream for further manufacturing steps.

The one or more servo motors 150 may be situated such that the arc paths of strip guides 102 occurs within in one or more planes. If the components are arranged such that the arc path of a strip guide 102 is substantially parallel with the plane which contains the nip line between joining rollers 201, 202, one mode of variation in the angle at which the strip material enters the nip is eliminated. Without intending to be bound by theory, it is believed that control over lateral shifting of the strip material and/or avoidance of roping are simplified and/or improved by such an arrangement.

Strip Guide and Guide Arm

An example of a strip guide 102 is depicted in perspective, side, front and rear views in FIGS. 6A, 6B, 6C and 6D, respectively. Strip guide 102 may be situated at or near the downstream end of strip guide arm 100. Strip guide arm 100 may extend from coupling collar 109.

In the example shown, strip guide 102, strip guide arm 100, and coupling collar 109 may be formed of aluminum alloy, and also may be integrally formed. Materials having a relatively high strength-to-weight ratio may be desirable in some circumstances. Examples of other suitable materials may include engineering plastics (such as polycarbonate thermoplastics, for example, LEXAN), aluminum, titanium alloys, thermoplastic or thermosetting resins reinforced with carbon fibers, graphite fibers, polyamide fibers, metal fibers and/or glass fibers, or other carbon fiber, graphic fiber, polyamide fiber, metal fiber and/or glass fiber composites.

Referring to FIGS. 6A and 6C, it can be seen that strip guide 102 may be formed to have an inner surface defining a U-shape, across which surface the strip material moves longitudinally. For purposes of this description, the term "U-shape" is to be broadly construed to include any two-dimensional figure lying within a plane with respect to a line within the plane, having either an intermediate straight portion along the line, or an intermediate curved portion to which the line is tangent, and two side portions each lying within the plane and on the same side of the line, and each extending from the intermediate portion in one or more directions away from the line. Where the intermediate portion is curved, the side portions may be continuous or discontinuous with such curve; thus, for example, an arc forming any portion of a circle falls within the definition of "U-shape" herein. By way of further example, the term includes a "C" shape, trough or open channel cross-sectional shape, horseshoe shape, etc. Unless otherwise specified the side portions need not terminate at a point of discontinuity. Thus, the term also includes, unless otherwise specified, any portion of a closed figure such as but not limited to a circle, oval, ellipse, rectangle, square, etc., that satisfies the foregoing definition. Symmetry about any particular axis is not intended to be implied or required unless otherwise specified. No limitation as to the spatial orientation of the U-shape with respect to other components of the system is implied or intended; for example, within the system the U-shape may be upside-down with respect to the letter "U"; see, e.g., strip guides 102 in FIG. 5.

Referring to FIG. 6C, in the example shown, the U-shape may have an intermediate portion 103 that substantially defines a semicircle, and two substantially straight side portions 104a, 104b. Without intending to be bound by theory, it is believed that an intermediate portion 103 of such shape may be more effective than other possible U-shapes for the purposes contemplated herein. It is believed that such substantially semicircular shape provides for easier and smoother lateral movement of strip material from side to side within strip guide 102 as strip guide arm 100 pivots back and forth during operation, allowing for better control over lateral shifting of the strip material, and better capability to prevent roping, than may be achieved with other possible shapes.

Still referring to FIG. 6C, strip guide 102 may have first and second strip edge stops 105a, 105b substantially terminating, or constituting substantially abrupt discontinuities, on side portions 104a, 104b. First and second strip edge stops 105a, 105b may extend from side portions 104a, 104b and inwardly toward each other, and may terminate at points short of each other to leave downstream strip insertion gap 108. First and second strip edge stops such as those shown at 105a, 105b may serve to retain a strip material within strip edge guide 102 during operation, preventing it from riding all the way up and off a side portion, and out of the strip guide.

Figure 7:
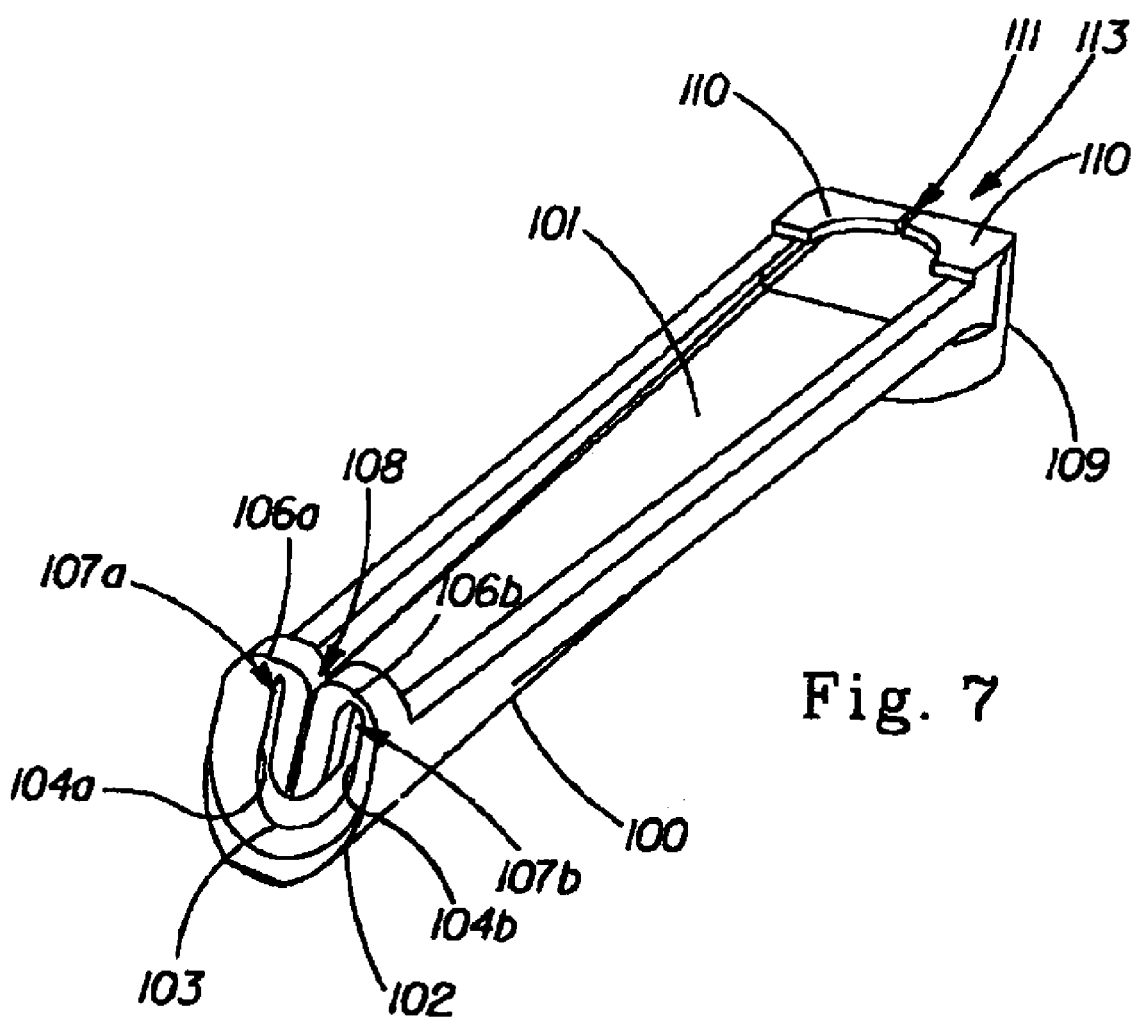
FIG. 7 is a perspective view of another embodiment of a strip guide arm.

Referring to FIG. 7, in another example strip guide 102 may have first and second strip edge guides 106a, 106b substantially terminating, or constituting substantially abrupt discontinuities, on side portions 104a, 104b. First and second strip edge guides 106a, 106b may extend from the ends of side portions 104a, 104b, inwardly toward each other, then toward intermediate portion 103, and then may terminate at points short of intermediate portion 103. In the example shown in FIG. 7, as with the example shown in FIG. 6A, there may be a downstream strip insertion gap 108 between first and second strip edge guides 106a, 106b. First and second strip edge guides such as those shown at 106a, 106b may serve to retain a strip material within strip edge guide 102 during operation, and also may be effective for providing additional assurance that longitudinal edges of a strip material do not longitudinally fold or flip over (rope) as the strip material shifts and rides up a side portion 104a, 104b during operation. The strip clearance 107a, 107b between the respective side portions 104a, 104b and respective strip edge guides 106a, 106b may be optimized to avoid unduly increasing friction resistance to longitudinal movement of the strip through the strip guide 102, while still having the desired effect of preventing the strip from roping. For example, if the strip material to be used is 2 mm thick, the strip guide 102 such as shown in FIG. 7 might be formed to have strip clearance 107a, 107b of, for example, approximately 2.5-3.5 mm.

Without intending to be bound by theory, it is believed that a strip guide such as strip guide 102 having strip edge guides such as those shown at 106a, 106b (FIG. 7) is more effective at preventing roping of strip than other embodiments lacking such strip edge guides. However, if the system for affixing the strip material to the substrate involves application of adhesive to the strip material upstream of the strip guide 102, edge guides wrapping over as shown might be deemed unsuitable in some circumstances, if they could become fouled with adhesive as the strip passes through the strip guide, or otherwise, could collect deposits of adhesive from the strip and randomly release them back onto the strip in unintended locations. Conversely, a strip guide having strip edge guides wrapping over, such as strip edge guides 106a and 106b, may be desirable in some circumstances, possibly such as when the system does not apply adhesive to the strip upstream of the strip guide.

As shown in the examples depicted in FIGS. 6A-6D and 7, at the upstream end of strip guide arm 100, two strip retainer extensions 110 may project from the edges of trough 101 inwardly toward each other, terminating short of each other to leave upstream strip insertion gap 111. Coupling collar 109 may have a substantially cylindrically-shaped drive shaft cavity 112 therein, as is indicated by dashed lines in FIGS. 6B and 6D.

The upstream and downstream strip insertion gaps 111, 108 provide for ease of lateral insertion of the strip material to be used into and along strip guide arm 100 during set-up. In another example, however, the respective strip retainer extensions 110 may be formed to meet, or be continuous to effectively constitute a single retainer structure, whereby the strip material must simply be longitudinally threaded thereunder, rather than laterally inserted through a gap, at set-up. Similarly, strip edge stops 105a, 105b (FIG. 6C) or strip edge guides 106a, 106b (FIG. 7) may be formed to meet, or be continuous, to effectively constitute a single strip retainer structure, whereby the strip material must simply be longitudinally threaded thereunder, rather than laterally inserted through a gap, at set-up.

As previously noted, without intending to be bound by theory, it is believed that a strip guide 102 may be more effective than other embodiments for the purposes contemplated herein if it includes an intermediate portion 103 (see, e.g., FIG. 6C) that substantially defines a semicircle. Without intending to be bound by theory, it is further believed that for the strip guide 102 to be more effective than other possible embodiments, the semicircle may have a radius $r_4$ of a length that is approximately 21-43 percent of the width of the strip material, or approximately 26-38 percent of the width of the strip material, or approximately 30-34 percent of the width of the strip material, or even approximately 32 percent of (or approximately $(1/\pi)$ times) the width of the strip material to be used. If $r_4$ is a length that is approximately 32 percent of (or approximately $(1/\pi)$ times) the width of the strip material to be used, the linear length of the arc formed by the semicircle is approximately equal to the width of the strip material. It is believed that a radius $r_4$ falling within one or more of these ranges may optimize the effect of the strip guide upon orientation of the respective longitudinal side edges of a strip as it enters the nip between a roller pair, striking a balance between most effective control over lateral shifting and minimizing the likelihood of roping and contour error.

Additionally, without intending to be bound by theory, it is believed that a strip guide 102 may be more effective if it has at least one side portion 104a and/or 104b joining the intermediate portion 103, than other possible embodiments not having such a side portion, for purposes such as those described herein. A side portion joining the intermediate portion at a side opposite the direction of lateral motion of the strip guide may provide additional guiding surface against which a strip material may ride during abrupt and/or severe changes in lateral position of the strip guide. The side portion may be substantially straight, and may be of a length that is approximately 21-61 percent of the width of the strip material, or approximately 26-56 percent of the width of the strip material, or approximately 30-52 percent of the width of the strip material, or even approximately 32-50 percent of the width of the strip material to be used. It is believed that such a dimension causes optimization of the orientation of the respective longitudinal side edges of a strip as it enters the nip between a roller pair, striking a balance between most effective control over lateral shifting and minimizing the likelihood of roping and contour error.

It is further believed that embodiments having two such side portions are more effective than embodiments with only one side portion, particularly if the strip material is to be shifted laterally to both sides of a line of entry of the strip material at the upstream end of the strip guide arm 100 (e.g., at upstream entry point 113). Expressed differently, when strip guide 102 is to move back and forth to points on both sides of the line of entry of the strip material at upstream entry point 113, two such side portions 104a, 104b may be desirable in some circumstances to improve control over the strip material.

During operation, as the strip guide 102 moves toward the limit of its lateral arc path to shift the strip laterally, the strip exits the strip guide at an increased lateral angle, creating a potential for friction lock, i.e., a point of unacceptably concentrated friction between the strip and the strip guide at the exit point as a result of tension in the strip. To mitigate this problem, in addition to having the above-described features, it may be desirable in some circumstances to shape the inside distal edges of the strip guide 102. The inside distal edges may be shaped such that they are chamfered, rounded or radiused, or even given a quarter-round transition, from inside surface to outside edge, to reduce friction between the strip guide 102 and the strip material as it passes longitudinally therethrough and exits the downstream end.

As noted, in the example shown strip guide 102 may be integrally formed with strip guide arm 100. Referring to FIG. 6A, strip guide arm 100 may form a trough 101, which on its inside surfaces may conform to the above-described U-shape at the downstream end, and gradually flatten out as it approaches the upstream (strip entry) end where strip guide arm 100 joins coupling collar 109. In another example, the strip guide arm may form a trough that does not substantially flatten out, but rather, has a depth from the strip guide to the upstream strip entry end, which may be substantially continuous. Because strip arm 100 may pivot back and forth such that strip guide 102 moves in an arc path back and forth about an axis (see FIG. 5) at a rate of approximately, for example, 7.5 cycles or more per second, a trough or other channel, conduit, tube or other suitable containing or retaining structure along the length of strip guide arm 100 may serve to contain the length of strip material 42 present along the length of strip guide arm 100 during such movement. Thus, such structure may provide additional inside surface area therealong that may serve to exert lateral force against strip material 42, working against the inertia or counter-momentum of the strip material and reducing a concentration of friction or binding of strip material 42 that may occur at strip guide 102 as strip guide 102 moves back and forth to effect rapid lateral shifting. Reduction of concentrations of friction may be desirable to reduce or avoid possible inconsistencies in the longitudinal strain of the strip material 42 as it is drawn into the joining mechanism.

Additionally, a trough or other channel, conduit, tube or other suitable containing, retaining and/or shielding structure along strip guide arm 100 may serve to shield the strip material from surrounding air and the resistance to lateral movement of the strip material 42 therethrough. Absent a shielding structure, friction with surrounding air may cause a free span of a typically pliable and relatively light, cloth-like strip material 42 to erratically and uncontrollably flip about and rope as the strip material is rapidly shifted laterally by strip guide 102.

In another example of a possible alternative to the upstream strip entry point 113 depicted in the Figures, the strip guide arm may have a upstream strip entry guide similar in design to the strip guide 102 but oriented in the opposite direction. This may provide further assurance against roping of the strip material. It also may serve to prevent or reduce increased friction or binding at the entry of strip material 42 into/onto strip guide arm 100 when strip guide arm pivots and introduces a varying angle in the path of the strip material, about the strip entry point. Again, avoidance or reduction of a concentration of friction at any particular point is desirable to avoid inconsistencies in the longitudinal strain of the strip material 42 as it is drawn into the joining mechanism.

It may be desirable in some circumstances that one or more of the surfaces of the strip guide 102, and other surfaces in or along strip guide arm 100 that contact the moving strip material, be polished to reduce friction between the strip material and such surfaces. This may include any of the inner surfaces of trough 101, strip edge stops 105a, 105b, strip edge guides 106a, 106b, strip entry point 113, strip retainer extensions 110, and any intermediate strip-contacting structures.

In addition, or as another possible measure, one or more of these surfaces may be coated with a low-friction coating, such as, for example, a fluoropolymer-based coating such as TEFLON, a product of E.I. du Pont de Nemours and Company, Wilmington, Del. Relative to the coefficient of friction provided by the strip guide/strip guide arm material without a coating, any suitable coating that lowers the coefficient of kinetic friction with the material of the outer surfaces of the strip material to be used may be selected. In another example, where an adhesive is to be applied to the strip material upstream of the strip guide arm 100 and/or strip guide 102, it may be desirable to coat strip-contacting surfaces of the strip guide arm 100 and/or strip guide 102 with an adhesive release coating. In another example, one or more inserts of a low-friction material conforming to the desired strip-contacting surface shape may be affixed on or within strip guide 102, strip guide arm 100, trough 101, strip edge stops 105a, 105b, strip edge guides 106a, 106b, strip entry point 113, strip retainer extensions 110, and any intermediate strip-contacting structures. Such inserts may be formed in whole or in part of low-friction materials such as, but not limited to, nylon, high density polyethylene, and fluoropolymer-based materials such as TEFLON.

In another example, a strip guide arm 100 and strip guide 102 may have some or all of the features and spatial arrangement with respect to a joining mechanism 200 as described above. However, rather than being connected to a servo motor, strip guide arm 100 may be connected at a pivot point to a stationary component, about which pivot point the strip guide arm 100 may pivot back and forth. In this example, strip guide arm 100 also may include a cam follower as part thereof, or connected thereto, which rides on a rotating cam directly or indirectly driven by a rotating driving mechanism, such as a rotary electric motor. The cam follower may be urged against the cam by any appropriate biasing mechanism, such as, but not limited to, one or more springs. The cam may be formed to have a profile such that by its rotation, strip guide arm 100 pivots as required to laterally shift strip material as required for the article being manufactured. The rotating driving mechanism may be operated so as to rotate the cam at a speed which is suitably associated with the speed at which the substrate material is moving.

In another example, a strip guide 102 having some or all of the features described above may be employed without a strip guide arm, servo motor, or the rotary operation described above. Rather, a strip guide may be connected to a linear movement mechanism such as, for example, a linear motor or actuator arranged to move the strip guide 102 along a line upstream and substantially parallel to the nip line between joining rollers 201, 202.

Figure 8:
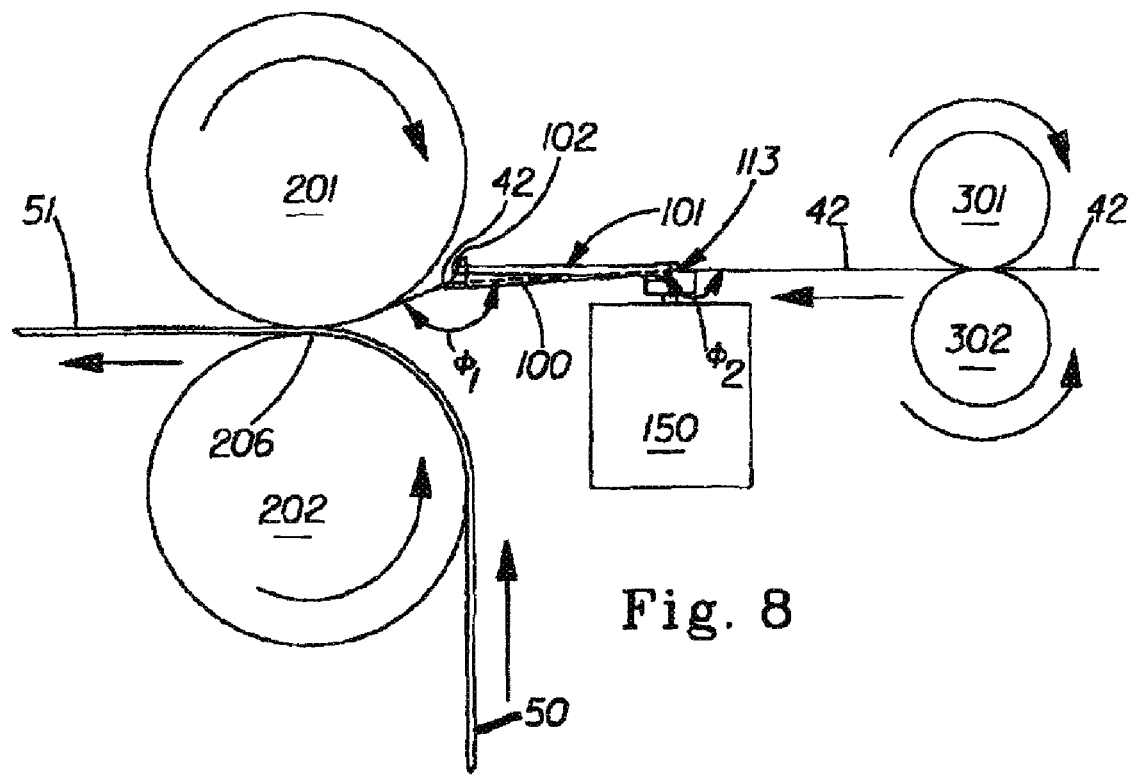
FIG. 8 is a schematic side view of a system including a feed mechanism, strip guide arm, servo motor, and joining mechanism, shown in the process of affixing a strip material to a sheet material.
Figure 9:
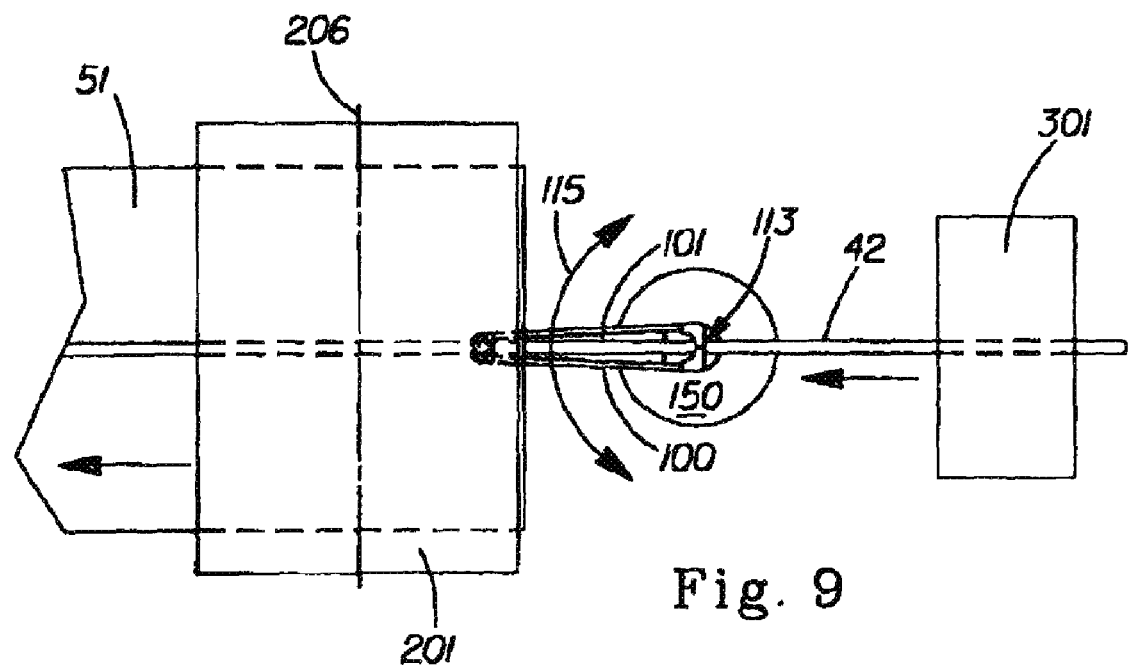
FIG. 9 is a schematic top view of a system including a feed mechanism, strip guide arm, servo motor, and joining mechanism, shown in the process of affixing a strip material to a sheet material.

Additional Strip Guide Design Features; Strip Guide Arm Dimensions, Location and Orientation Referring to FIGS. 8 and 9, where a joining mechanism including rollers such as first and second joining rollers 201, 202 is used, decreasing the distance between strip guide 102 and the nip line 206 between joining rollers 201, 202 sharpens the possible angle α (the angle reflecting a lateral break in the line of placement of the strip material 42 on a substrate material relative to the machine direction (see, e.g., FIG. 3), that can be achieved. Constraints on closeness of this distance may include the physical dimensions of the servo motor and joining mechanism/rollers used and limits on the length of the strip guide arm, discussed further below. If a joining roller 201, 202 has a radius of about 7.62 cm, it may be desirable in some circumstances to arrange the components so that the distal edge of strip guide 102 is less than about 2 cm from nip line 206. Depending upon features and sizes of the components used, it may be possible in some circumstances to arrange the components such that the ratio of the distance between distal edge of strip guide 102 and the nip line to the radius of the smaller of the rollers that strip guide 102 faces, is less than about 0.34, or less than about 0.31, or less than about 0.29, or even less than about 0.26.

As the arranged distance between the distal edge of strip guide 102 and the nip line is decreased as constraints permit, it may become desirable in some circumstances to form strip guide 102 so as to have a radiused concave profile as viewed from a side, having radius $r_3$ (see FIG. 6B). Radius $r_3$ may originate at the axis of one of first or second joining rollers 201, 202, such that the concave side profile of strip guide 102 is concentric with the joining roller 201 or 202 that it faces. This enables the distal tip of the strip guide 102 to be located closer to the nip line, while avoiding interference between the other portions of the strip guide 102 and the roller it faces.

Under certain circumstances forces created by air entrainment or other factors may tend to lift strip material 42 from the inner surfaces of strip guide 102, reducing the efficacy of strip guide 102. Still referring to FIGS. 8 and 9, it may be desirable in some circumstances to arrange servo motor 150 with mounted strip guide arm 100 such that strip material 42 passing along strip guide arm 100 forms a first break angle $\phi_1$ between its path along strip guide arm 100 and its path from strip guide 102 to the nip line between joining rollers 201, 202 (see FIG. 8). First break angle $\phi_1$, combined with tension in the strip material 42, may help assure that strip tension-related forces urge strip material 42 into strip guide arm 100 and strip guide 102 (downwardly with respect to FIG. 8), and hold strip material 42 against the inside surfaces thereof. For similar reasons, it may be desirable in some circumstances to arrange a servo motor 150 with mounted strip guide arm 100, and/or the supply source of strip material 42, such that strip material 42 passing along strip guide arm 100 forms a second break angle $\phi_2$ between its path from the upstream strip material feed (e.g., feed rollers 301, 302) and its path along strip guide arm 100 (see FIG. 8). In one example, second break angle $\phi_2$ may be designed into and formed as a feature of strip guide arm 100, trough 101 thereof and/or the interface between upstream strip entry point 113 and trough 101. One or both of break angles $\phi_1$ and $\phi_2$ may be kept within a range of about 135-179 degrees, or about 151-173 degrees, or about 159-170 degrees, or even about 167 degrees. Without intending to be bound by theory, it is believed that, depending upon factors which may include the coefficient of kinetic friction between the strip material and the strip guide surfaces, a break angle $\phi_1$ or $\phi_2$ smaller than about 135 degrees may be too sharp, i.e., it could possibly result in an unacceptable concentration of friction between strip material 42, strip guide 102 and/or upstream strip entry point 113 as strip material 42 passes thereover. Further, without intending to be bound by theory, it is believed that optimization of break angles $\phi_1$ and $\phi_2$ will be affected by the modulus of elasticity of the strip material, the longitudinal strain or tension in the strip material as it passes along strip guide arm 100, the lateral stiffness or "beam strength" of the strip material, the width of the strip material, and the linear speed of the strip material as it passes along strip guide arm 100.

Figure 10:
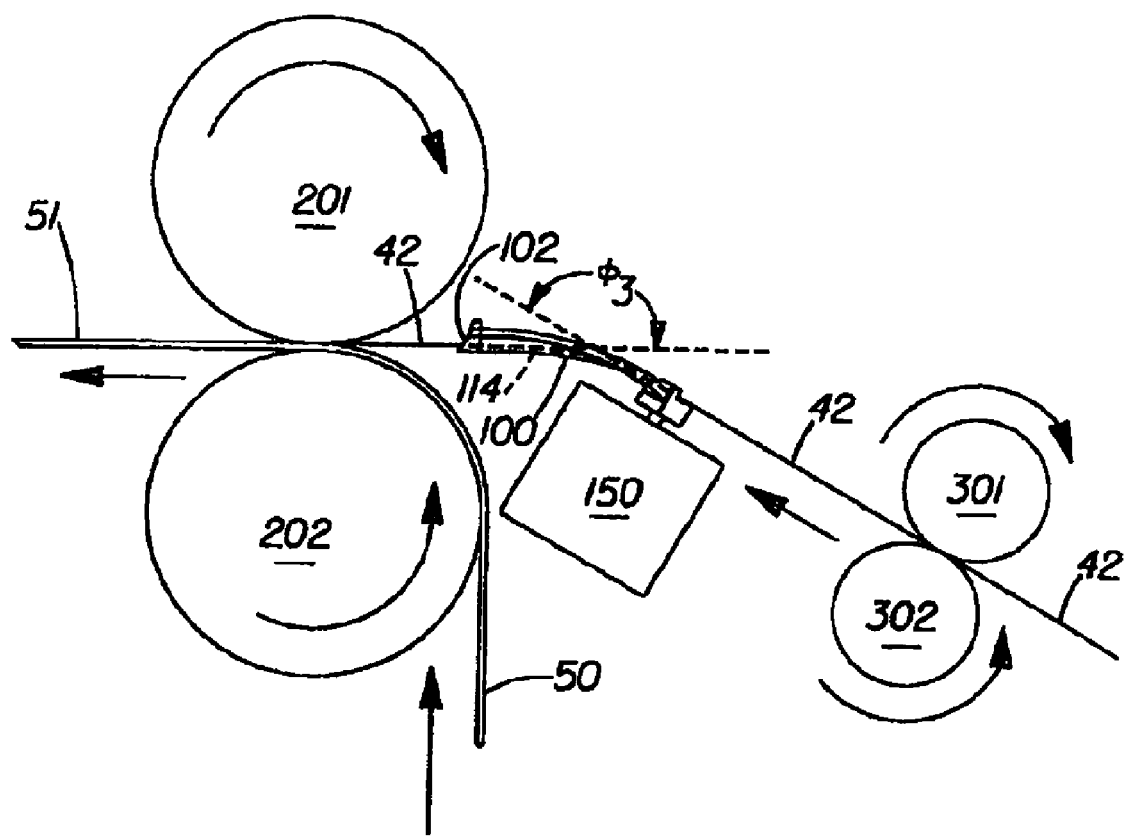
FIG. 10 is a schematic side view of a system including a feed mechanism, another embodiment of a strip guide arm, servo motor, and joining mechanism, shown in the process of affixing a strip material to a sheet material.

Referring to FIG. 10, in another embodiment and as an alternative to being formed and arranged to create discrete break angles $\phi_1$ and $\phi_2$, strip guide arm 100 may be designed and formed so as to provide a curving strip guide arm path 114 therethrough, which diverges away (with reference to FIG. 10, downwardly) from the incoming strip material path when the other components are appropriately arranged. The components may be arranged such that the total break angle $\phi_3$ between the incoming strip path (upstream of where strip material 42 contacts strip guide arm 100) and the exiting strip path (downstream of where strip material breaks contact with strip guide 102) is from about 90-178 degrees, or about 122-166 degrees, or about 138-160 degrees, or even about 154 degrees. Such a total break angle $\phi_3$, combined with tension in the strip material, may help improve the likelihood that strip tension-related forces urge strip material 42 against inside surfaces of the described curving strip guide arm path 114 (with reference to FIG. 10, along the bottom surfaces inside strip guide arm 100).

In some circumstances it may be desirable that the length of the strip guide arm 100 is as great as possible. As the strip guide arm 100 is made longer, the arc path of the strip guide 102 in front of nip line 206 approaches that of a line. As such a linear path is approached, the potential sharpness of a lateral shift of the strip material in front of the nip line is increased. However, the torque load capacity of any servo motor, and the material strength of any strip guide arm, will have limits. These factors are sources of constraints on the design length of the strip guide arm 100. Torque load on the servo motor in the arrangement of components described herein will be at its maximum when the most rapid change in direction and/or speed of rotation (highest angular acceleration/deceleration) is imposed by the design of the finished product (i.e., the most abrupt angular acceleration/deceleration required of the strip guide arm will impose the greatest torque load). If the torque load capacity of a servo motor is exceeded, the precision of rotation of the servo motor drive shaft may deviate unacceptably from that required by the associated programming, and the servo motor may even fail. Additionally, as a strip guide arm 100 mounted to the drive shaft of a servo motor is made longer and/or heavier along its length, angular inertia and angular momentum become greater. As a result, angular acceleration/deceleration require greater torque, imposing greater demand on the servo motor. Bending/shear stress along the length of the strip guide arm also increases with increasing angular acceleration/deceleration and angular inertia/momentum, increasing the probability of strip guide arm material failure. Related constraints are imposed by the line speed and the resulting cycling speed demanded of the servo motor, and by the magnitude and abruptness of the change in lateral placement of the strip material, a function of the design of the article being manufactured. Another related constraint is imposed by the weight of the strip material that is being handled by the strip guide arm, which adds to lateral inertia and momentum which must be overcome to effect lateral shifting. Many or all of the above-discussed design considerations will be affected by the particular design of the article to be manufactured, which will involve a particular profile of location and affixation of a strip material to a substrate material at laterally varying locations on the substrate material.

Effects of Described Components and Features

Figure 11A:
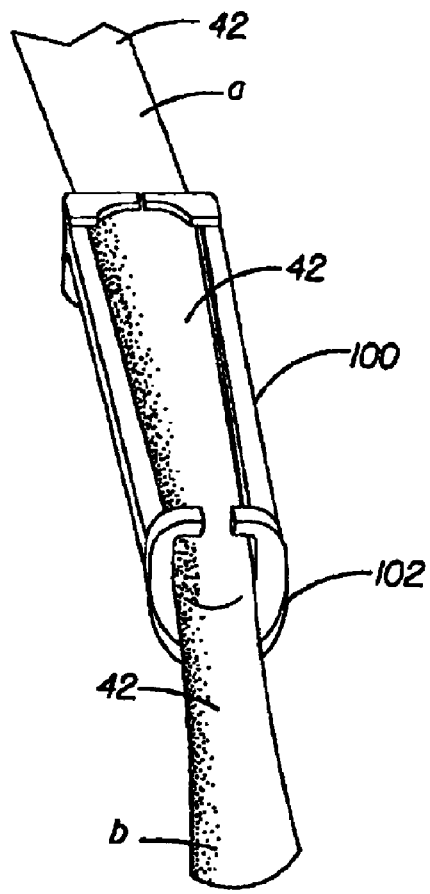
FIGS. 11a and 11b are perspective views of a strip guide arm in two differing positions, respectively, shown with strip material lying therealong.
Figure 11B:
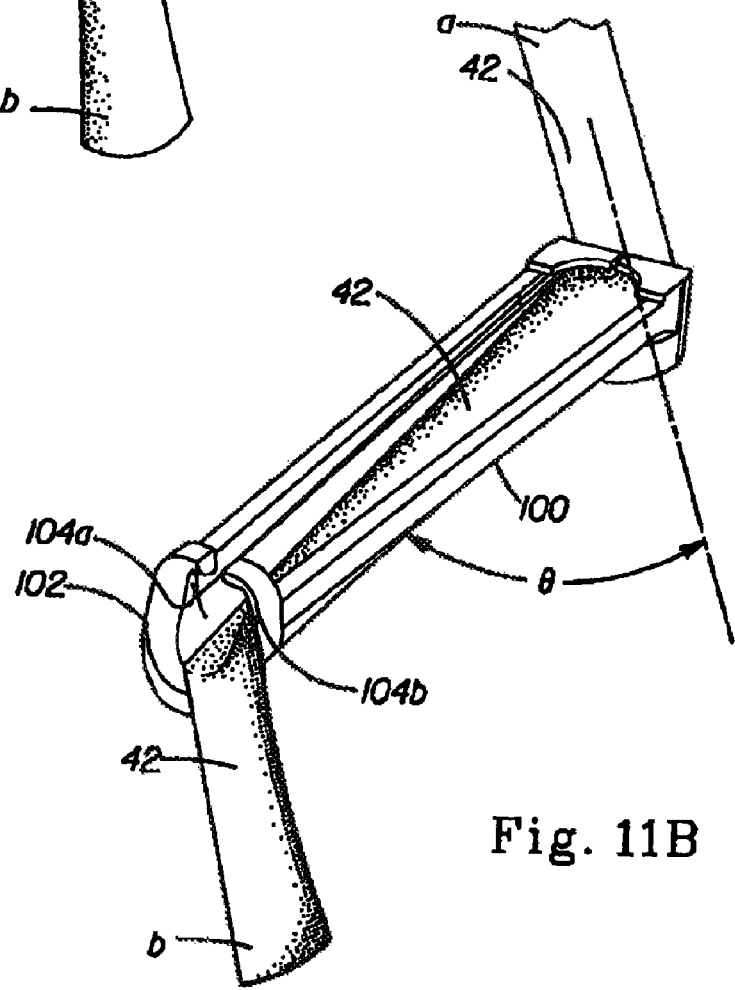

Certain effects and advantages provided by components and features described above are discussed with reference to FIGS. 11A-11D. FIG. 11A illustrates a strip guide arm 100 with strip guide 102 situated at the distal end thereof (similar to that shown in FIGS. 6A-6D) having strip material 42 threaded therethrough, these components represented isolated, but otherwise as they might appear in a system within the scope of present invention. FIG. 11A depicts an arrangement with a substantially straight strip path (viewed from above) from point a to point b. When the path of strip material 42 as viewed from above is substantially straight, pliable strip material 42 enters proximal entry point 113 in substantially flat condition, then gradually flexes across its width so as to rest in concave fashion in and against the surfaces of the intermediate portion of strip guide 102. In FIG. 11B, strip guide arm 100 is shown pivoted clockwise by an angle θ, as it might be pivoted in operation in a system in order to effect lateral shifting of strip material 42. With pivoting of strip guide arm 100, strip material 42 tends to move and ride up along the side portion 104b that is situated opposite the direction of rotation (relative to FIG. 11B, to the right of strip guide 102). Correspondingly, the right edge of strip material 42 (relative to FIG. 11B) is raised and the left edge is lowered. The strip material does not tend to rope.

Figure 11C:
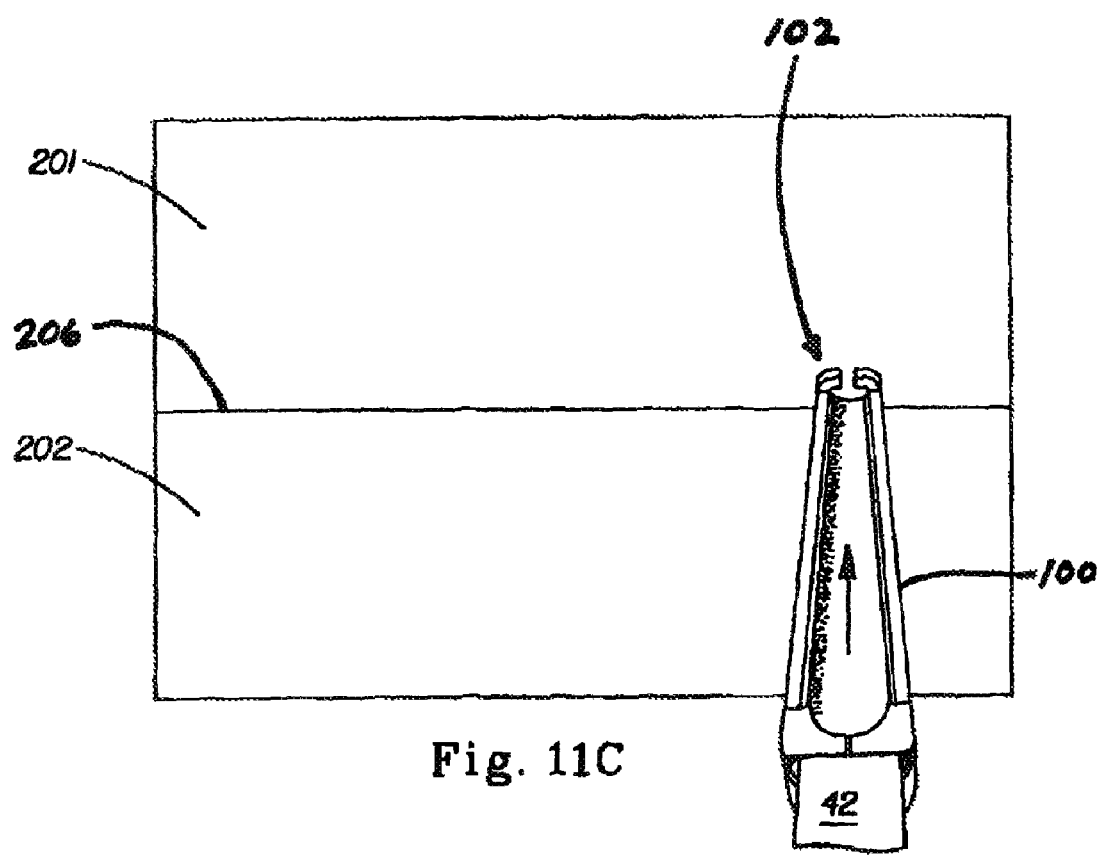
FIGS. 11c and 11d are perspective views of a system including a strip guide arm in two differing positions, respectively, shown with strip material lying therealong and moving therethrough, and downstream toward a pair of joining rollers.
Figure 11D:
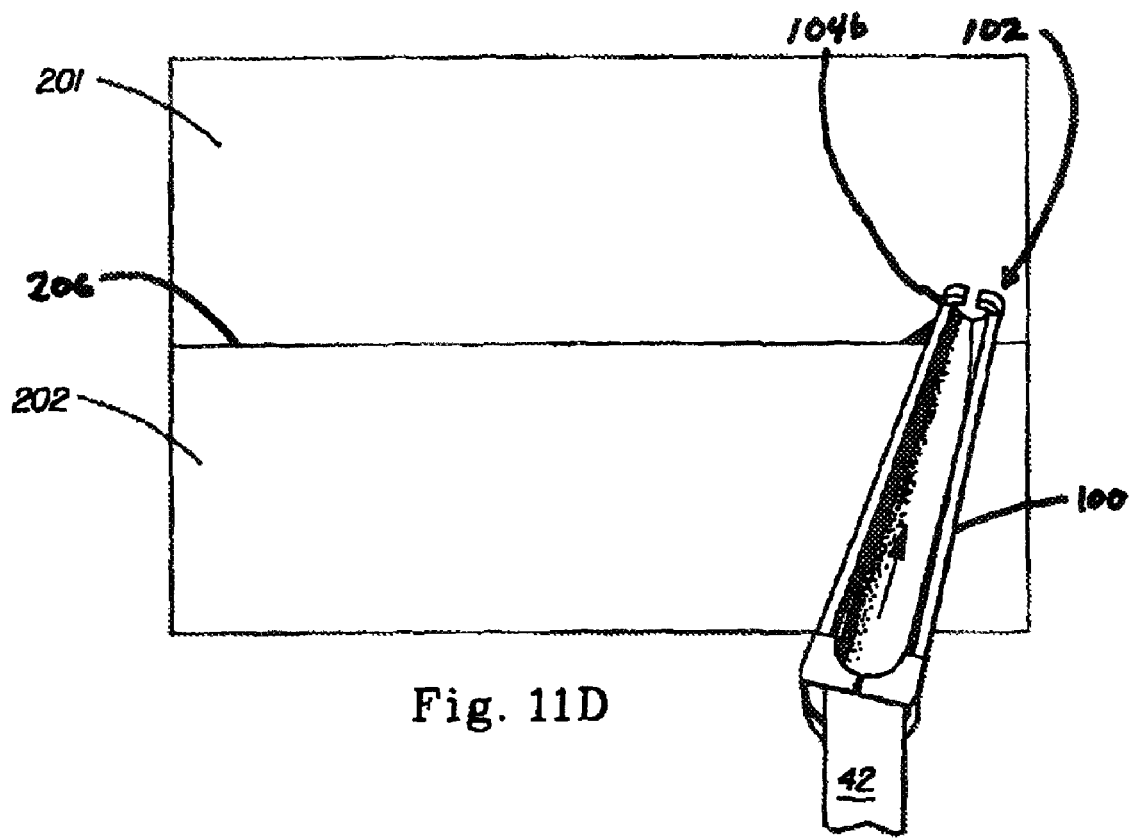

FIGS. 11C and 11D are views of the strip guide arm 100 shown in FIGS. 11A and 11B from the opposite perspective of that of FIGS. 11A and 11B, as strip guide arm 100 may appear operating as a component of a system. FIGS. 11C and 11D show how strip guide 102 affects entry of the strip material 42 into the nip 206 between joining rollers 201, 202. In FIG. 11C, the path of strip material 42 moving toward joining rollers 201, 202 is substantially straight, as in FIG. 11A. As it moves along strip guide arm 100 and through strip guide 102, strip material 42 may be urged by the inside surfaces of strip guide arm 100 and/or strip guide 102 into a concave shape across its width, and may enter the nip between joining rollers 201, 202 with each of its side edges upturned (with respect to the view in FIG. 11A). However, roping of strip material 42 may be avoided, and strip material 42 is then flattened against the substrate as it passes through the nip. Referring to FIG. 11D, when strip guide arm 100 pivots clockwise and strip guide 102 moves to the right (relative to FIG. 11D), strip material 42 may shift to the left of the strip guide 102, riding up the left inside surface and up side portion 104b of strip guide 102. Strip material 42 may approach the nip between joining rollers 201, 202 in a concave shape across its width, with its left side edge higher and its right side edge lower (with respect to the view in FIG. 11C). As a result, the upturned left side edge may contact upper joining roller 201 before the remaining width of the strip does, but then be urged down and flattened by joining roller 201 as the strip material 42 enters the nip. Strip guide 102 acting in combination with the joining rollers 201, 202, may thereby enable strip material 42 to be drawn into and compressed at the nip without roping. Thus, strip material 42 may be caused to emerge from the downstream side of the nip affixed to the substrate material in a flat condition.

Thus, a system having one or more of the features described above may be used to manufacture a portion of wearable article such as that shown in FIG. 1, having respective leg openings circumscribed by legbands 40, each formed of a single length of elastic strip material, which substantially encircles its leg opening. The backsheet 20 may comprise a nonwoven web material. For each legband 40 the single length of elastic strip material encircling the same may be bonded to the nonwoven web material via compression bonding.

Strip Strain Regulation

As previously noted, in one example of a design of a product such as wearable article 10 and the manufacture thereof, the design may call for the longitudinal straining of the strip material prior to the affixing thereof to a substrate sheet material. In some circumstances it may be desirable to provide a system for introducing and regulating the amount of strain of the strip material prior to its entry into a joining mechanism.

Figure 12:
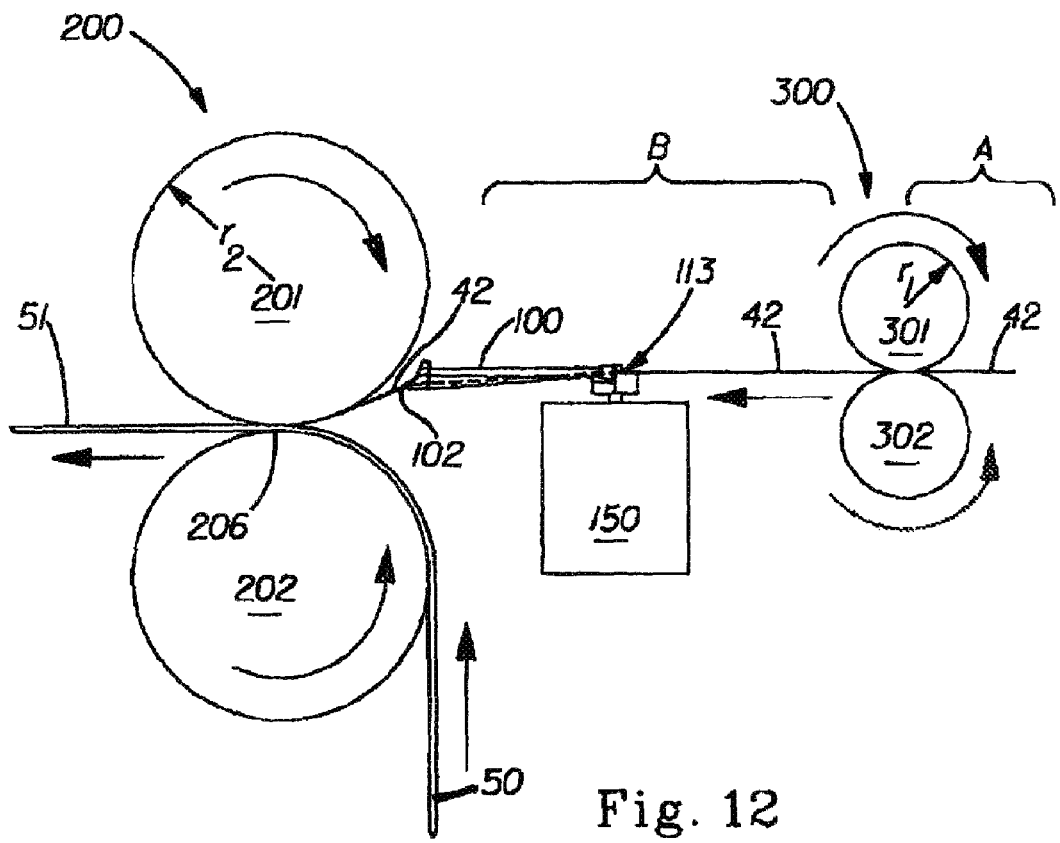
FIG. 12 is a schematic side view of a system including a feed mechanism, strip guide arm, servo motor, and joining mechanism, shown in the process of affixing a strip material to a sheet material.
Figure 13:
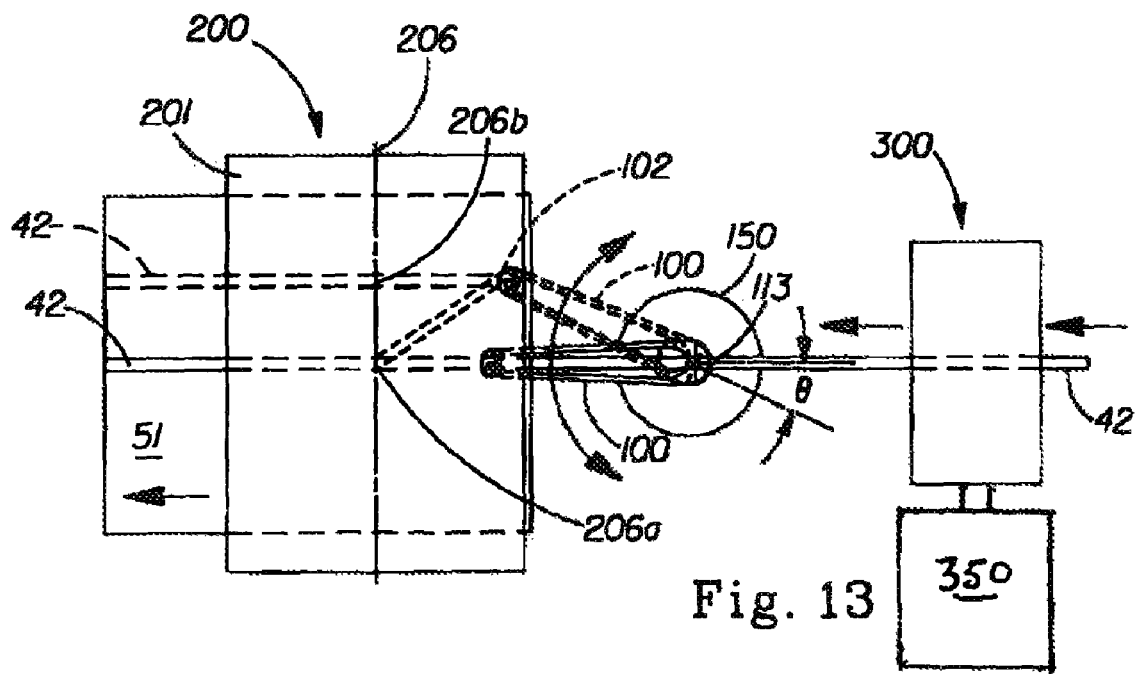
FIG. 13 is a schematic top view of a system including a feed mechanism, strip guide arm, servo motor, and joining mechanism, shown in the process of affixing a strip material to a sheet material.

An example of a strain regulation system is schematically depicted in FIGS. 12 and 13. The example may include the joining mechanism 200 with first and second joining rollers 201, 202, and a strain regulation mechanism 300 that may include first and second feed rollers 301, 302. Feed rollers 301, 302 may substantially non-slippably draw and feed incoming strip material 42 in a downstream direction as indicated by the arrows. One or both of feed rollers 301, 302 may have a circumferential surface of a compressible elastic material such as a natural or synthetic polymeric material, for example, rubber. This may help avoid damage to the strip material 42 (from compressing it beyond the limits of its elasticity) as it passes through the nip between feed rollers 301, 302. Additionally a rubber or rubber-like material may be provided that provides a coefficient of friction between the strip material 42 and the feed roller surface that is sufficient to avoid longitudinal slippage of the strip material 42 through the nip. It may be desirable in some circumstances to locate feed rollers 301, 302 as closely as possible to upstream strip entry point 113. This will minimize the overall length of the path of the strip material 42 from the nip between feed rollers 301, 302 to the joining mechanism, and thus, facilitate more precise control over strain in the strip material 42.

To longitudinally strain incoming strip material 42 prior to bonding to incoming backsheet material 50, feed rollers 301, 302 may be caused to rotate at a speed whereby the linear speed of the circumferential surfaces of feed rollers 301, 302 is slower than the linear speed of the circumferential surfaces of joining rollers 201, 202 of joining mechanism 200. If $r_1$ is the radius of feed roller 301 (in meters) and $\omega_1$ is the rate of rotation of feed roller 301 (in rotations/second), the linear speed $V_1$ of its circumferential surface is:

$$V_1 = 2\pi r_1 \omega_1 \text{ meters/second},$$

which will be the linear strip feed speed through the nip between feed rollers 301, 302.

Similarly, if $r_2$ is the radius of joining roller 201 (in meters) and $\omega_2$ is the rate of rotation of joining roller 201 (in rotations/second), the linear speed $V_2$ of its circumferential surface is:

$$V_2 = 2\pi r_2 \omega_2 \text{ meters/second},$$

which is the linear strip draw speed through the nip between rollers 201, 202.

Strain will be introduced into the strip material 42 if $V_1$ is less than $V_2$ and strip material 42 does not substantially slip longitudinally as it passes through the respective nips between respective roller pairs 301, 302 and 201, 202. Thus, referring to FIG. 12, strip material 42 may be drawn from zone "A" in a substantially non-strained condition by feed rollers 301, 302 at a linear feed speed slower than the linear strip draw speed of joining rollers 201, 202. As a result, the strip material 42 in zone "B" will be strained prior to its entry into joining mechanism 200.

Thus, if a design for an article calls for longitudinally straining the strip material to strain $\epsilon$ ($\epsilon$=change in length/relaxed length; where $\epsilon$ is expressed as a percentage) prior to bonding to the substrate material, relative speeds $V_1$ and $V_2$ will provide for the required strain $\epsilon$ if:

$$(1+\epsilon)V_1 = V_2, \text{ or}$$

$$V_2/V_1 = (1+\epsilon),$$

assuming a constant length of the path of the strip material from the feed mechanism to the joining mechanism. Accordingly, for example, to impart 70% strain to the strip material as it is affixed to a substrate material, the respective feed rollers 301, 302 and joining rollers 201, 202 may be operated such that $V_2/V_1 = 1.70$, assuming a constant length of the path of the strip material from the feed mechanism to the joining mechanism.

In the event, however, that the length of the path of the strip material from the feed mechanism to the joining mechanism is subjected to change, strain of the strip material in zone "B" will undergo an associated transient elevation or dip. If the change in path length is substantial and abrupt enough, it is possible that the strain in the strip material may be caused to transiently elevate or dip substantially. Examples of a system as described herein shift a strip material path laterally prior to its entry into a joining mechanism, to cause affixation of the strip material to a substrate material in laterally varying locations on the substrate material. This lateral shifting causes change in the length of the path of the strip material from the feed mechanism to the joining mechanism. A change of this nature may be substantial and abrupt enough to substantially vary strain of the strip material in zone "B".

Figure 14:
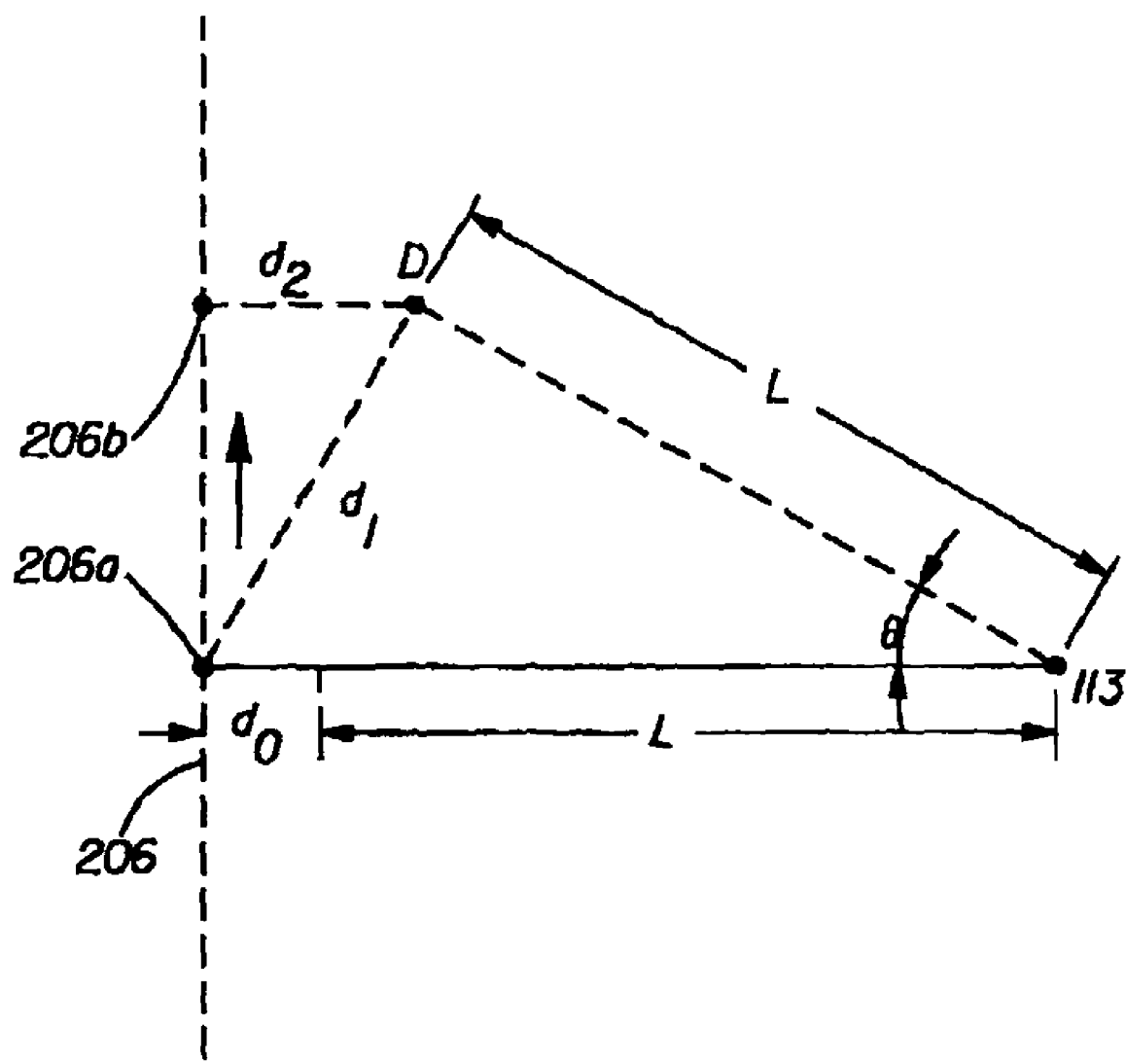
FIG. 14 is a geometric schematic diagram illustrating examples of strip path lengths varying as a result of pivoting of a strip guide arm.

FIGS. 13 and 14 show that the path of the strip material 42 from upstream strip entry point 113 to first nip point 206a has a first path length in zone "B" when strip guide arm 100 is oriented with its longitudinal axis substantially perpendicular to nip line 206. The first path length is approximately the sum of the length L of strip guide arm 100 plus distance $d_0$ from strip guide 102 to nip point 206a.

Pivoting of strip guide arm 100 by an angle θ causes an increase in the path length. The increase reaches an initial peak in the path length, which approaches the sum of strip guide arm length L plus the distance $d_1$ from strip guide displacement point D to first nip point 206a, as speed of rotation by angle θ approaches infinity (pivoting of arm 100 approaches instantaneous). The increase then settles back from the initial peak to a second path length, as the nip point between joining rollers 201, 202 shifts as indicated by the arrow in FIG. 14 from first nip point 206a to second nip point 206b by continuing rotation of joining rollers 201, 202. The second path length will be approximately the sum of strip guide arm length L plus the distance $d_2$ from strip guide displacement point D to second nip point 206b. The second path length, while less than the peak, remains greater than the first path length.

With $V_1$ and $V_2$ held constant, a path length increase will not necessarily cause a substantial elevation in strain. Through the continuous feeding and drawing of strip material through zone "B" by roller pairs 301, 302 and 201, 202, the system continuously corrects an elevation or dip in strain, always asymptotically seeking the strain determined by the values of $V_1$ and $V_2$ (see equations immediately above). Accordingly, in some circumstances the system may effectively regulate and maintain substantially consistent strain despite changes in path length. The time required for the system to substantially correct a transient elevation in strain resulting from an increase in path length is dependent upon the total length of the strip material path in zone "B" and the values of $V_1$ and $V_2$. Thus, if pivoting of strip guide arm to angle θ is relatively slow and gradual, the system may be able to effectively "keep up," continuously seeking initial strain, and any transient elevation in strain may be relatively slight.

As the pivoting of strip guide arm by angle θ becomes more rapid, however, the system may become unable to effectively "keep up" and maintain strain within an insubstantial margin of elevation over initial strain. Thus, it is possible that a relatively rapid pivoting of strip guide arm through angle θ may cause a substantial elevation in the strain of strip material in zone "B".

The foregoing describes only one possible example of circumstances in which strain in strip material 42 may vary as a result of a change in pivot angle θ. There may be other circumstances in which elevations and even dips in strain may be caused. For example, still referring to FIGS. 12-14, there may be circumstances in which pivot angle θ is at a maximum, the nip point is at 206b, and the system has stabilized to initial strain. If pivot angle θ is then decreased, the decrease will cause a dip in the strain in the strip material in zone "B" below its initial value as strip guide 102 moves past nip point 206b, followed by an elevation as strip guide 102 moves away from nip point 206b (downwardly with reference to FIGS. 13 and 14). Again, if the pivoting of the strip guide arm through these positions is relatively rapid, the corresponding dip or elevation in strain could become substantial.

One example of the potential effect of such a transient elevation in strain is explained with reference to FIGS. 15A-D.

Figure 15A:
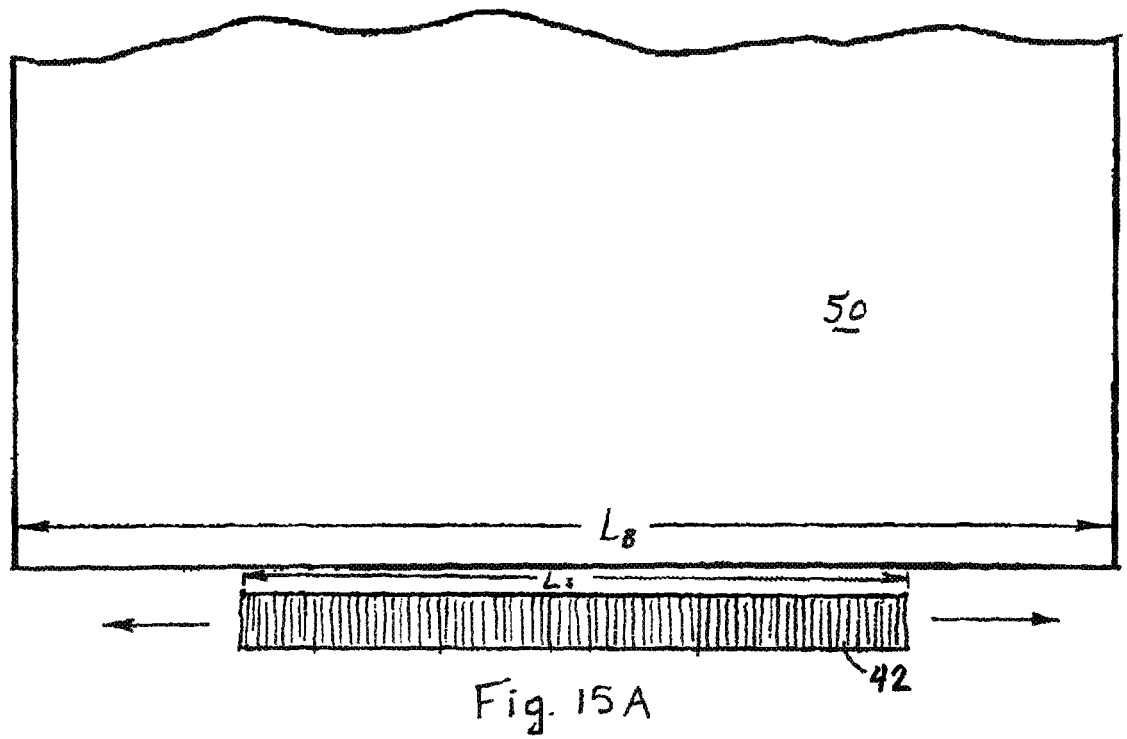
FIG. 15A is a schematic plan view of respective portions of a substrate material and an elastic strip material, shown unruffled and relaxed, respectively.
Figure 15B:
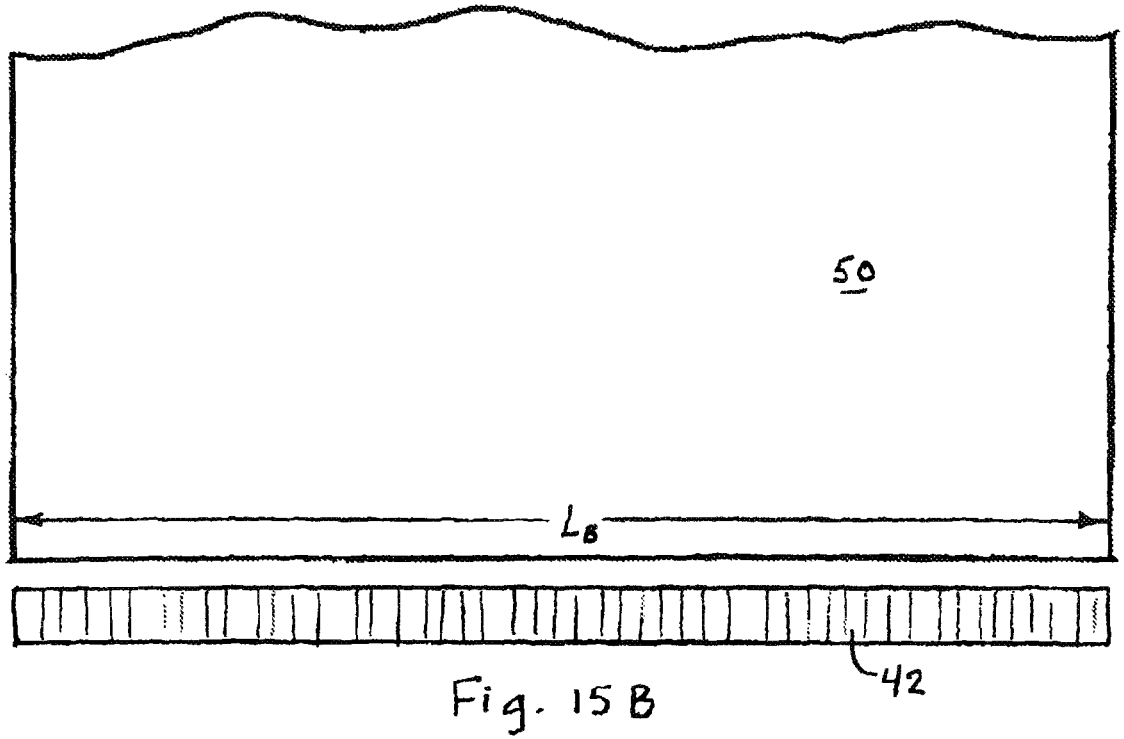
FIG. 15B is a schematic plan view of respective portions of a substrate material shown unruffled and an elastic strip material shown in a strained condition.
Figure 15:
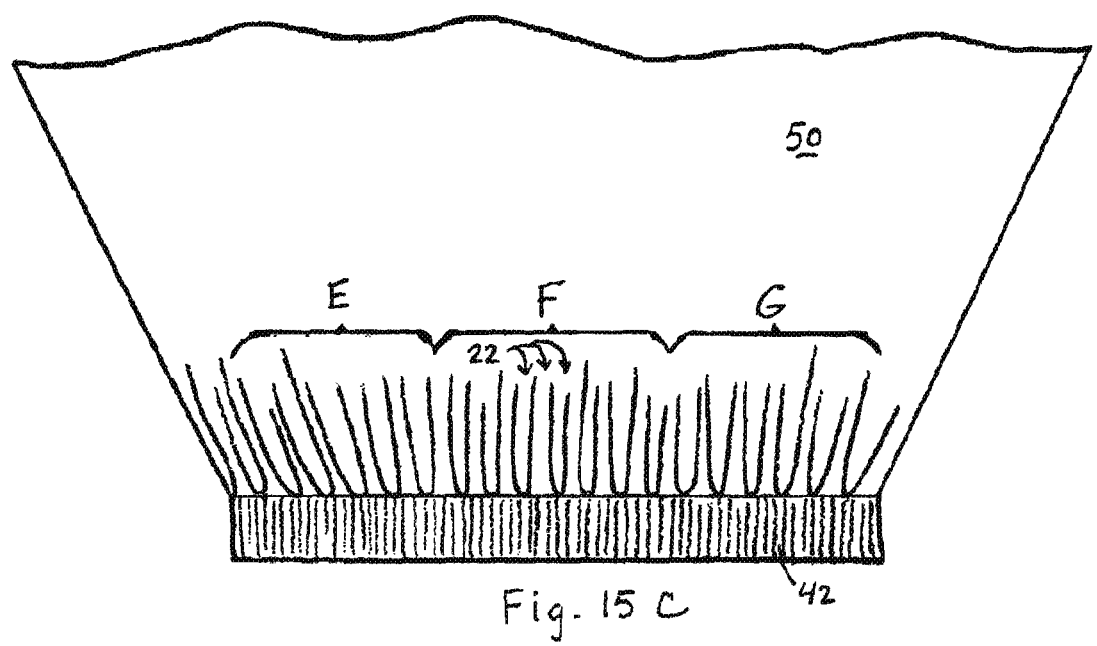
FIG. 15C is a schematic plan view of a portion of a substrate material shown with rugosities along an affixed portion of an elastic strip material in a relaxed condition.
FIG. 15D is a schematic plan view of a portion of a substrate material shown with rugosities along an affixed portion of an elastic strip material in a relaxed condition.
Figure 15:
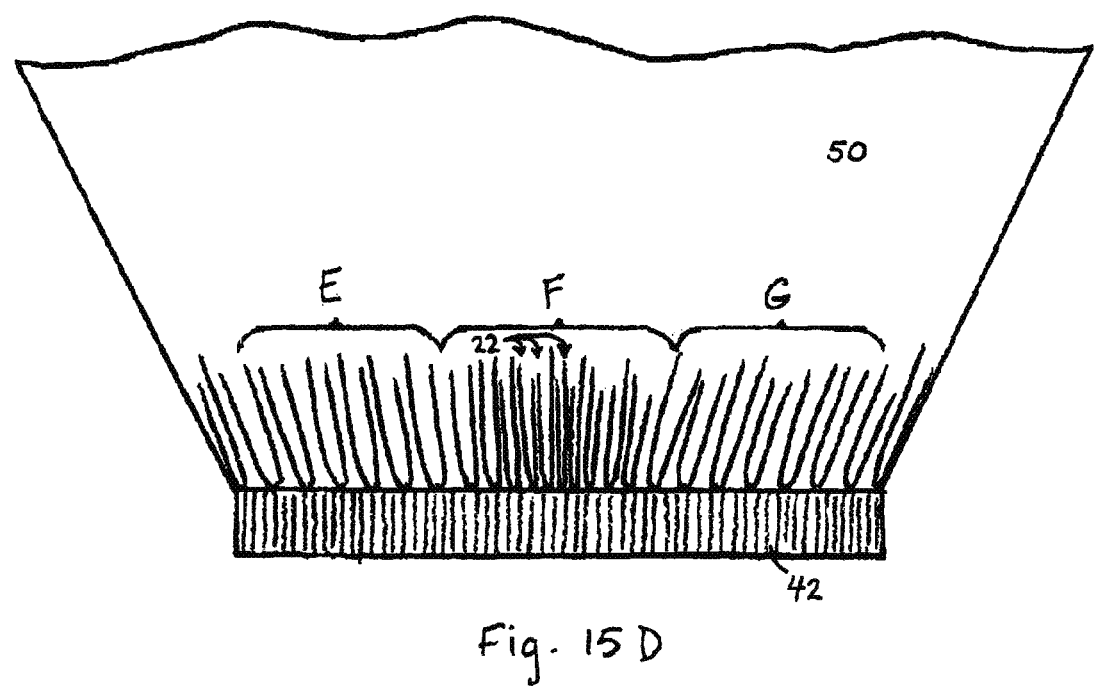

Referring to FIG. 15A, a system having some or all of the features described above may be arranged and set up to apply a relaxed length $L_s$ of elastic strip material 42 to a length $L_B$ of flat, unruffled substrate material such as backsheet material 50. The system may be designed to cause the strip material 42 to be longitudinally strained prior to application, as indicated by the arrows. In the strained condition as shown in FIG. 15B, strip material 42 is then applied and affixed to backsheet material 50 along length $L_B$.

Following such application, strip material 42 may be allowed to relax. Elastic strip material 42 will seek to return to its relaxed length $L_s$, and the affixed backsheet material 50 will develop transverse rugosities 22, along strip material 42 as depicted in FIG. 15C. Transverse rugosities 22 consist of gathered backsheet material affixed along relaxed strip material 42. If, prior to application, strip material 42 is under uniform and constant strain, the flat, unruffled length $L_B$ of backsheet material 50 will be approximately evenly distributed along the relaxed length $L_s$ of strip material 42, gathered in the rugosities 22. The rugosities 22 may appear generally evenly distributed in either quantity or size, or a combination thereof. Assuming consistency in respective material dimensions and properties, each of regions "E", "F" and "G" as depicted in FIG. 15C generally will have approximately equal linear quantities of backsheet material 50 gathered and bonded along strip material 42.

If, however, the strain in strip material 42 is varied as it is being affixed to the backsheet material, the unruffled length $L_B$ of backsheet material 50 may not be evenly distributed along the relaxed length of strip material 42 after affixation, and relaxation. For example, referring to FIG. 15D, if there was an elevation in the strain in strip material 42 in region "F" as it was applied to backsheet material 50, region "F" may have a linear quantity of backsheet material 50 bonded along strip material 42 per relaxed unit length of strip material 42, that is greater than in either of adjacent regions "E" or "G". As depicted in FIG. 15D, this may manifest itself in a greater number of rugosities 22 per relaxed unit length of strip material in region "F" as compared to the adjacent regions "E" and "G". Another possible manifestation is that the rugosities 22 in region "F" may be greater in size than those in the adjacent regions.

In some circumstances involving such variation in strain, the linear quantity of backsheet material gathered along strip material in a first region, per relaxed unit length of strip material, may be, for example, approximately 125 percent, approximately 150 percent, approximately 175 percent, approximately 200 percent, or even more, than that in one or more adjacent regions. This may evidence that the strain of the elastic strip material as it was applied to the substrate material with the substrate material in flat, unruffled condition, was greater in the first region than in the one or more adjacent regions, by roughly corresponding percentages. In a product such as a finished wearable article wherein the strip material encircles a leg opening, this may manifest itself in a discontinuity or variation in the gathering of material about a leg opening.

Referring again to FIGS. 12-14, it is possible that substantial variations of strain in the strip material 42 in zone "B" may in some circumstances be deemed undesirable and unacceptable. In the example described immediately above, variations of strain in the strip material as it is affixed to the backsheet material may result in leg openings with discontinuity or variation in the gathering of material thereabout. In some circumstances this might be deemed to unacceptably compromise product quality, appearance, fit or comfort. In other applications, specifications may call for relatively small variance in strain, if not substantially constant strain, of strip material. Thus, it may be desirable in some circumstances to compensate for abrupt variations in strip path length in order to continuously regulate amount of strain in the strip material 42 in zone "B", before and as it enters joining mechanism 200.

Such compensation may be provided by use of a feed servo motor 350 driving one or both of feed rollers 301, 302. In one example, one of feed rollers 301, 302 may be driven by a feed servo motor, and the other of feed rollers 301, 302 may be a passive, idling roller. Referring to FIGS. 12 and 13, the programming of servo motor 150 will be designed to cause the system to locate and apply the strip material 42 to the backsheet material 50 along the profile required by the article design. Thus, the programming will contain information concerning the timing and magnitude of angle θ by which the strip guide arm 100 is pivoted back and forth on a cyclic basis. This information can be used to program cyclic adjustments to the rotational speed of feed rollers 301, 302 (and thus, $V_1$) to avoid unacceptable variance of the strain of the strip material 42 in zone "B". Generally, in the example depicted, a rate of increase or decrease in the path length in zone "B" has the same effect as would an increase or decrease in the linear strip draw speed through the nip between rollers 201, 202. To avoid unwanted variations in strain, this increase or decrease may be offset by an equivalent increase or decrease of the linear strip feed speed through the nip between feed rollers 301, 302.

For example, while angle θ is increasing, the strip path length is growing and $V_1$ may be temporarily increased in accordance with the rate of increase in the path length, which can mitigate or avoid an unacceptable elevation in strain of strip material 42 in zone B.

At any time period in which angle θ may dwell at a relatively constant value (as may be required by a particular article design), the strip path length also becomes constant, i.e., the rate of increase or decrease in the path length in zone "B" becomes zero. In this event the system would cause strain in the strip material to approach the strain determined by the initial values of $V_1$ and $V_2$, and $V_1$ may be returned to its pre-adjustment initial value to maintain substantially constant strain of the required design (initial) value.

If after a dwell and substantial stabilization, angle θ decreases from a peak value abruptly enough to cause an unacceptable dip in strain below initial design value, a compensating adjustment may be made. Thus, while angle θ decreases from a peak, $V_1$ may be temporarily decreased in accordance with the rate of decrease in the path length, which can mitigate or avoid an unacceptable dip in the strain of strip material 42 in zone B.

The requirement for such correction, and the programming of the feed servo motor 350 driving feed rollers 301, 302 to regulate strain in the manner described above, will be directed by factors including the design features and specifications of the particular product being manufactured, the speed of the joining mechanism 200 and/or rollers 201, 202, the programming of servo motor 150, the distance between the feed nip and the upstream strip entry point 113, the length of the strip guide arm 100, and the distance between the distal end of strip guide 102 and joining nip line 206.

A strain regulation/adjustment mechanism such as the example described above may be used for purposes other than maintenance of consistent strain. There may be circumstances in which it is desirable to intentionally vary strain. For example, referring to FIG. 3, it can be seen that portions of strip material 42 affixed to partially completed portion 51 may be wasted because they occupy areas of completed portion 51 that are to be cut away from the portion that forms outer chassis 28 (FIG. 2). In order to minimize waste and conserve strip material, strain of strip material 42 in these waste areas may be increased, thereby reducing the quantity of strip material that is affixed in the waste areas. A strain regulation/adjustment mechanism such as the example described above may be programmed to increase strain in the strip material as it enters the nip between joining roller pair 201, 202 in locations in such waste areas, and then return the strain to product design strain as the strip material enters the nip to be affixed in non-waste areas.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A strip guide for laterally shifting a longitudinally moving strip material as it enters a joining mechanism that urges the strip material into contact with a moving sheet material, the strip guide comprising a surface over which the strip material passes longitudinally, the surface defining a U-shape, wherein the U-shape has a curving portion that substantially comprises a semicircle having a radius, and the strip material has a strip width, and the radius of the semicircle is approximately 21 to approximately 43 percent of the strip width.

2. The strip guide of claim 1 wherein the U-shape has at least one substantially straight side portion adjoining the semicircle, the side portion having a length, the length being approximately 21 to approximately 61 percent of the strip width.

3. The strip guide of claim 2 wherein the U-shape has two substantially straight side portions adjoining the semicircle, the side portions having a length, the length being approximately 21 to approximately 61 percent of the strip width.

4. The strip guide of claim 1 wherein the U-shape comprises an intermediate portion and two side portions each adjoining the intermediate portion, and each respective side portion terminates at a respective strip edge guide.

5. The strip guide of claim 1 wherein the U-shape comprises an intermediate portion and two side portions each adjoining the intermediate portion, and each respective side portion terminates at a respective strip edge stop.

* * * * *